(12) United States Patent
Olson et al.

(10) Patent No.: US 10,500,348 B2
(45) Date of Patent: Dec. 10, 2019

(54) PALM ACTIVATED DRUG DELIVERY DEVICE

(71) Applicant: Janssen Biotech, Inc., Malvern, PA (US)

(72) Inventors: Lorin Olson, Scotts Valley, CA (US); Vaclav Vojan, Pizen (CZ); Juergen Ernst Pfrang, Kallmuenz (DE); Peter Krulevitch, Pleasanton, CA (US); Jingli Wang, San Jose, CA (US); Nicholas Foley, Edinburgh (GB); Mingqi Zhao, San Jose, CA (US); Paul Tashjian, Phoenixville, PA (US)

(73) Assignee: Janssen Biotech, Inc., Malvern, PA (US)

( * ) Notice: Subject to any disclaimer, the term of this patent is extended or adjusted under 35 U.S.C. 154(b) by 401 days.

(21) Appl. No.: 14/959,701

(22) Filed: Dec. 4, 2015

(65) Prior Publication Data
US 2016/0089503 A1  Mar. 31, 2016

Related U.S. Application Data

(60) Division of application No. 13/833,978, filed on Mar. 15, 2013, now Pat. No. 9,233,213, which is a
(Continued)

(51) Int. Cl.
*A61M 5/32* (2006.01)
*A61M 5/315* (2006.01)
(Continued)

(52) U.S. Cl.
CPC ............ *A61M 5/326* (2013.01); *A61M 5/315* (2013.01); *A61M 5/3129* (2013.01);
(Continued)

(58) Field of Classification Search
CPC .. A61M 5/326; A61M 5/3243; A61M 5/3287; A61M 5/3213; A61M 2005/3247;
(Continued)

(56) References Cited

U.S. PATENT DOCUMENTS

| 3,742,948 A | 7/1973 | Post et al. |
| D323,032 S | 1/1992 | McCrary |

(Continued)

FOREIGN PATENT DOCUMENTS

| EP | 1483004 B1 | 12/2004 |
| EP | 1621222 A1 | 2/2006 |

(Continued)

OTHER PUBLICATIONS

U.S. Appl. No. 29/449,399, filed Mar. 15, 2013, Foley et al.
(Continued)

*Primary Examiner* — Bhisma Mehta
*Assistant Examiner* — Hamza A Darb
(74) *Attorney, Agent, or Firm* — BakerHostetler

(57) ABSTRACT

A device configured to administer a medication can comprise a lower housing that includes a housing latch. The device can further comprise a needle guard that is movable relative to the lower housing along a first direction from a first position to a second position so as to expose a needle, and an upper housing supported relative to the lower housing. The upper housing can be configured to move with respect to the lower housing along a second direction from a pre-use position to a dispensed position. The housing latch can releasably interfere with the upper housing when the upper housing is in the pre-use position so as to prevent the upper housing from moving toward the dispensed position, and the movement of the needle guard toward the second
(Continued)

position, causes the interference to be removed, thereby allowing the upper housing to move toward the second position.

20 Claims, 37 Drawing Sheets

Related U.S. Application Data continuation-in-part of application No. 12/905,572, filed on Oct. 15, 2010, now Pat. No. 9,216,256.

(60) Provisional application No. 61/361,983, filed on Jul. 7, 2010, provisional application No. 61/252,378, filed on Oct. 16, 2009.

(51) Int. Cl.
*A61M 5/31* (2006.01)
*A61M 5/50* (2006.01)
*A61M 5/20* (2006.01)

(52) U.S. Cl.
CPC ...... *A61M 5/31511* (2013.01); *A61M 5/3213* (2013.01); *A61M 5/3243* (2013.01); *A61M 5/3287* (2013.01); *A61M 5/50* (2013.01); *A61M 5/20* (2013.01); *A61M 5/2033* (2013.01); *A61M 5/2046* (2013.01); *A61M 5/2053* (2013.01); *A61M 5/3157* (2013.01); *A61M 5/3204* (2013.01); *A61M 5/5086* (2013.01); *A61M 2005/208* (2013.01); *A61M 2005/2013* (2013.01); *A61M 2005/2026* (2013.01); *A61M 2005/2073* (2013.01); *A61M 2005/3123* (2013.01); *A61M 2005/3125* (2013.01); *A61M 2005/3126* (2013.01); *A61M 2005/3247* (2013.01); *A61M 2205/581* (2013.01); *A61M 2205/582* (2013.01); *A61M 2205/583* (2013.01); *A61M 2205/584* (2013.01); *A61M 2205/586* (2013.01)

(58) Field of Classification Search
CPC ........ A61M 5/3204; A61M 2005/3125; A61M 5/3129; A61M 5/315; A61M 2005/3126; A61M 2005/3123; A61M 5/3157; A61M 2205/583; A61M 2205/584; A61M 2205/582; A61M 2205/581; A61M 5/20; A61M 2005/2026; A61M 5/5086; A61M 2005/208; A61M 5/2053; A61M 5/2046; A61M 2005/2013; A61M 5/2429; A61M 5/283

See application file for complete search history.

(56) References Cited

U.S. PATENT DOCUMENTS

| | | |
|---|---|---|
| 5,271,527 A | 12/1993 | Haber et al. |
| 5,295,965 A | 3/1994 | Wilmot |
| 5,378,233 A | 1/1995 | Haber et al. |
| 5,540,664 A | 7/1996 | Wyrick |
| 5,795,336 A | 8/1998 | Romano et al. |
| 5,873,856 A | 2/1999 | Hjertman et al. |
| 5,938,642 A | 8/1999 | Burroughs et al. |
| 5,957,896 A | 9/1999 | Bendek et al. |
| D418,917 S | 1/2000 | Duchon et al. |
| D428,650 S | 7/2000 | Bellhouse et al. |
| 6,183,446 B1 | 2/2001 | Jeanbourquin |
| 6,221,046 B1 | 4/2001 | Burroughs et al. |
| 6,235,004 B1 | 5/2001 | Steenfeldt-Jensen et al. |
| 6,547,764 B2 | 8/2003 | Gullak et al. |
| D485,365 S | 1/2004 | Py et al. |
| D488,382 S | 4/2004 | Calello |
| 6,726,657 B1 | 4/2004 | Dedig et al. |
| D491,275 S | 6/2004 | Walters et al. |
| 6,743,205 B2 | 6/2004 | Nolan et al. |
| 6,805,686 B1 | 10/2004 | Fathallah et al. |
| 6,808,507 B2 | 10/2004 | Roser |
| D510,139 S | 9/2005 | Gilad et al. |
| 6,986,760 B2 | 1/2006 | Giambattista et al. |
| 7,011,649 B2 | 3/2006 | De La Serna et al. |
| 7,074,211 B1 | 7/2006 | Heiniger et al. |
| 7,112,187 B2 | 9/2006 | Karlsson |
| D533,457 S | 12/2006 | Snyder |
| D548,336 S | 8/2007 | Galbraith |
| 7,252,651 B2 | 8/2007 | Haider et al. |
| D559,396 S | 1/2008 | Dave |
| 7,314,464 B2 | 1/2008 | Giambattista et al. |
| D562,987 S | 2/2008 | Colin et al. |
| D567,388 S | 4/2008 | Harold et al. |
| 7,361,160 B2 | 4/2008 | Hommann et al. |
| D577,814 S | 9/2008 | Seki et al. |
| D596,744 S | 7/2009 | Hull et al. |
| 7,585,287 B2 | 9/2009 | Bresina et al. |
| D612,487 S | 3/2010 | Hunter et al. |
| D613,400 S | 4/2010 | Hunter et al. |
| D613,401 S | 4/2010 | Hunter et al. |
| D613,861 S | 4/2010 | Hunter et al. |
| 7,744,565 B2 | 6/2010 | Heiniger et al. |
| D619,720 S | 7/2010 | Cheetham |
| D623,738 S | 9/2010 | Van der Stappen |
| D627,459 S | 11/2010 | Uchida et al. |
| D633,199 S | 2/2011 | MacKay et al. |
| 7,918,824 B2 | 4/2011 | Bishop et al. |
| D644,516 S | 9/2011 | Howell et al. |
| D644,529 S | 9/2011 | Padain et al. |
| D647,613 S | 10/2011 | Paget et al. |
| D677,382 S | 3/2013 | Foley |
| D678,514 S | 3/2013 | Foley |
| D697,205 S | 1/2014 | Schneider et al. |
| D719,650 S | 12/2014 | Arinobe et al. |
| 9,216,256 B2 | 12/2015 | Olson et al. |
| 9,233,213 B2 | 1/2016 | Olson et al. |
| 9,352,099 B2 * | 5/2016 | Roberts et al. |
| 2002/0004648 A1 * | 1/2002 | Larsen .................. A61M 5/326 604/195 |
| 2003/0229314 A1 * | 12/2003 | McWethy ............. A61M 5/326 604/197 |
| 2004/0019326 A1 | 1/2004 | Gilbert et al. |
| 2005/0085839 A1 | 4/2005 | Allen et al. |
| 2005/0222539 A1 | 10/2005 | Gonzales et al. |
| 2005/0273061 A1 | 12/2005 | Hommann et al. |
| 2006/0142691 A1 | 6/2006 | Trautman et al. |
| 2006/0189938 A1 | 8/2006 | Hommann et al. |
| 2006/0229569 A1 | 10/2006 | Lavi et al. |
| 2006/0270984 A1 | 11/2006 | Hommann et al. |
| 2006/0270985 A1 | 11/2006 | Hommann et al. |
| 2007/0016142 A1 | 1/2007 | Burren et al. |
| 2007/0173770 A1 | 7/2007 | Stamp |
| 2008/0154200 A1 | 6/2008 | Lesch |
| 2008/0228147 A1 | 9/2008 | David-Hegerich et al. |
| 2009/0292257 A1 | 11/2009 | Barrelle et al. |
| 2009/0299295 A1 | 12/2009 | Rubinstein et al. |
| 2009/0318864 A1 * | 12/2009 | Carrel .................. A61M 5/326 604/117 |
| 2010/0292653 A1 | 11/2010 | Maritan |
| 2011/0092915 A1 | 4/2011 | Olson et al. |
| 2013/0204229 A1 | 8/2013 | Olson et al. |
| 2013/0331796 A1 | 12/2013 | Wozencroft |
| 2014/0303564 A1 | 10/2014 | Roberts |
| 2016/0058955 A1 | 3/2016 | Olson et al. |
| 2016/0089503 A1 | 3/2016 | Olson et al. |

FOREIGN PATENT DOCUMENTS

| | | |
|---|---|---|
| EP | 1888149 | 2/2008 |
| EP | 1703929 | 10/2009 |
| EP | 2488237 | 8/2012 |
| EP | 2588166 A1 | 5/2013 |
| EP | 2588167 A1 | 5/2013 |
| EP | 2588168 B1 | 5/2013 |

(56) References Cited

FOREIGN PATENT DOCUMENTS

| | | |
|---|---|---|
| EP | 2646101 A4 | 10/2013 |
| EP | 2654854 A2 | 10/2013 |
| EP | 2661293 A1 | 11/2013 |
| EP | 2667914 A1 | 12/2013 |
| EP | 2667915 A1 | 12/2013 |
| EP | 2694141 A1 | 2/2014 |
| EP | 2907537 A1 | 8/2015 |
| FR | 2770404 | 5/1999 |
| FR | 2884722 | 10/2006 |
| FR | 2905273 | 3/2008 |
| JP | H05-245197 A | 9/1993 |
| JP | H07-136263 A | 5/1995 |
| JP | 2005-530565 | 10/2005 |
| JP | 2007-0117438 | 5/2007 |
| JP | 2008-0220949 | 9/2008 |
| JP | 2008-0536597 | 9/2008 |
| JP | 2009-060982 | 3/2009 |
| JP | D1431935 | 1/2012 |
| JP | 2013-508032 | 3/2013 |
| JP | 2013520214 A | 6/2013 |
| KR | 10-2006-0129024 | 12/2006 |
| KR | 10 2009-0025305 A | 3/2009 |
| MX | 2007009152 | 3/2008 |
| UA | 2012/10236 | 10/2012 |
| UA | 2014/01074 | 4/2014 |
| UA | 110026 | 11/2015 |
| WO | WO 2002/32484 | 4/2002 |
| WO | WO 2004/000395 A1 | 12/2003 |
| WO | 2005/058396 A1 | 6/2005 |
| WO | WO 2005/070481 A1 | 8/2005 |
| WO | WO 2005/113039 A1 | 12/2005 |
| WO | WO 2006/079064 | 7/2006 |
| WO | 2006/083876 A2 | 8/2006 |
| WO | WO 2006/111859 | 10/2006 |
| WO | WO 2006/111864 | 10/2006 |
| WO | WO 2006/117691 | 11/2006 |
| WO | WO 2006/129196 | 12/2006 |
| WO | WO 2008/005315 A2 | 1/2008 |
| WO | WO 2008/10738 | 9/2008 |
| WO | WO 2009/095805 | 8/2009 |
| WO | WO 2010/017650 | 2/2010 |
| WO | WO 2010/146358 A2 | 12/2010 |
| WO | WO 2011/047298 | 4/2011 |
| WO | WO2011/101383 A1 | 8/2011 |
| WO | WO 2011/101383 A1 | 8/2011 |
| WO | 2011/109205 A2 | 9/2011 |
| WO | 2012/000834 A1 | 1/2012 |
| WO | WO 2012/093071 A1 | 7/2012 |
| WO | 2013/032779 A2 | 3/2013 |

OTHER PUBLICATIONS

International Patent Application No. PCT/US2010/052894: International Search Report dated Jan. 31, 2011, 4 pages.

Zosano Pharma, "ZP-PTH Lead Product", http://www.zosanopharma.com/index.php?option=com_content&Task=view&id=27&Itemid=167, Jun. 2, 2011, 2 pages.

"Self-Injection Technologies Self Dose Injector Platform Technology", West Pharmaceutical Inc., https://web.archive.org/web/20121016052111/http://www.westpharma.com/en/products/pages/selfdose.aspx, Oct. 16, 2012, 1 page.

* cited by examiner

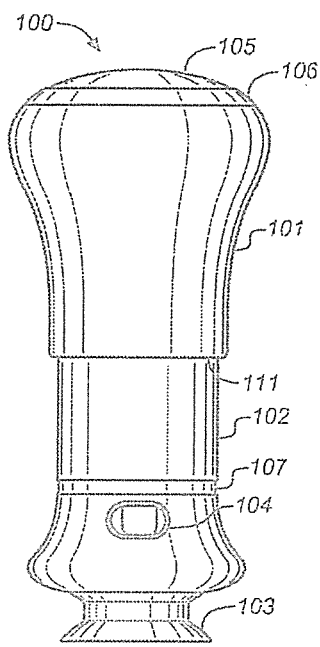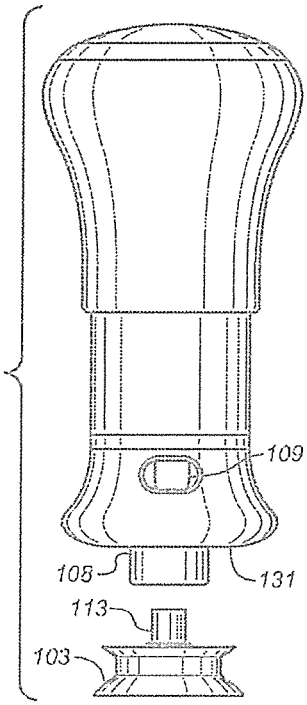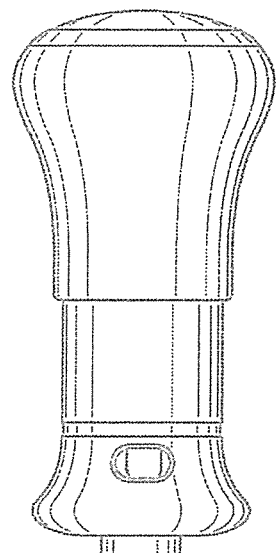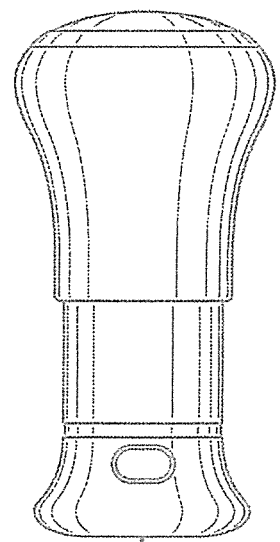

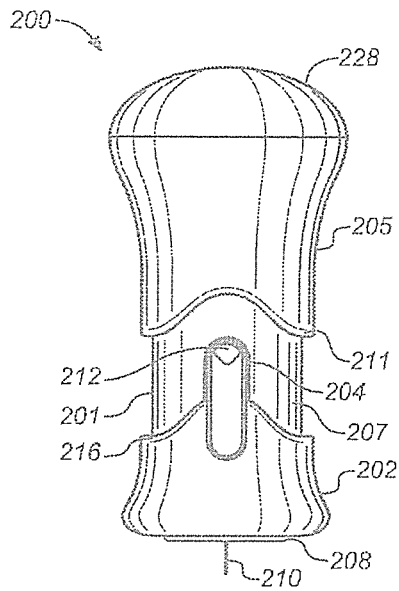
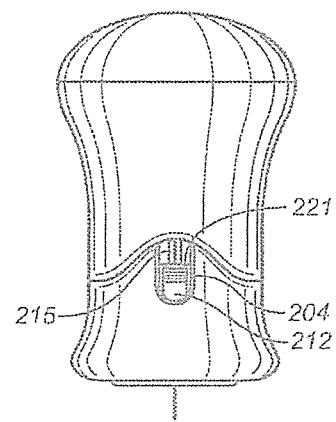
FIG. 11A  FIG. 11B
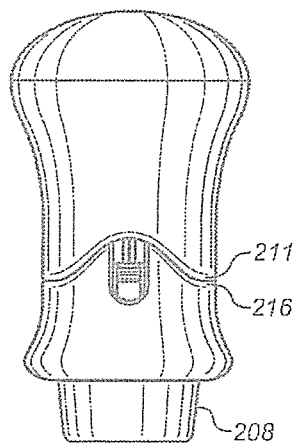
FIG. 11C

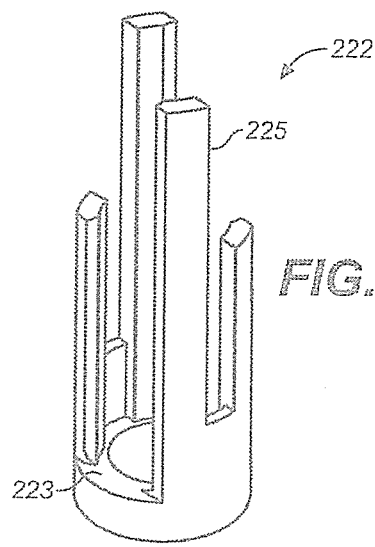
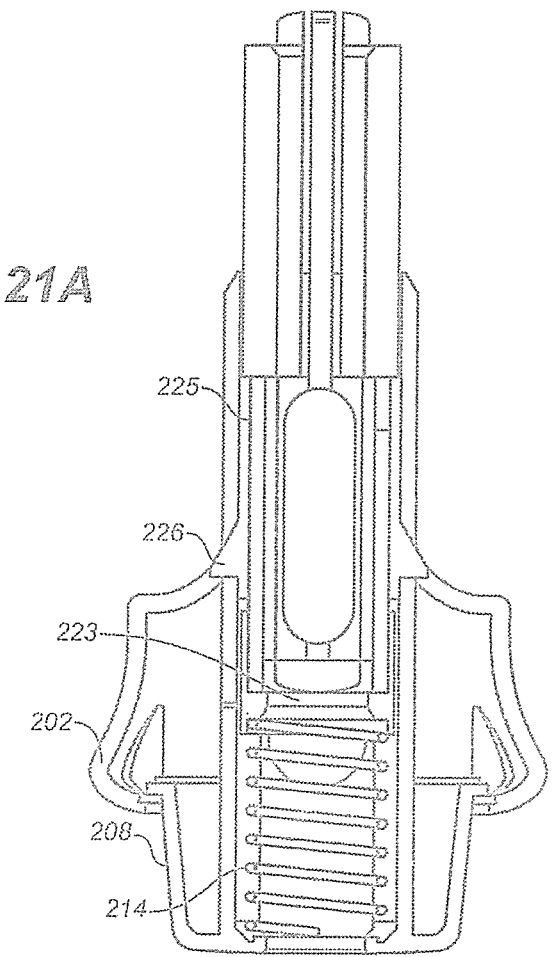
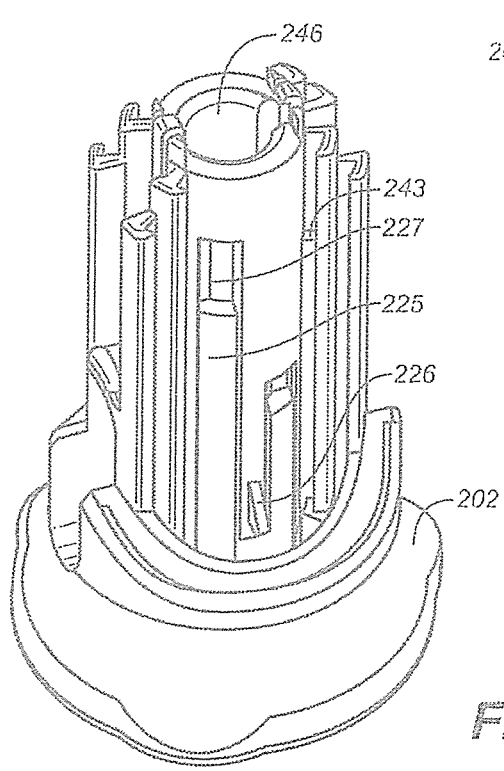
FIG. 21A
FIG. 21C
FIG. 21B

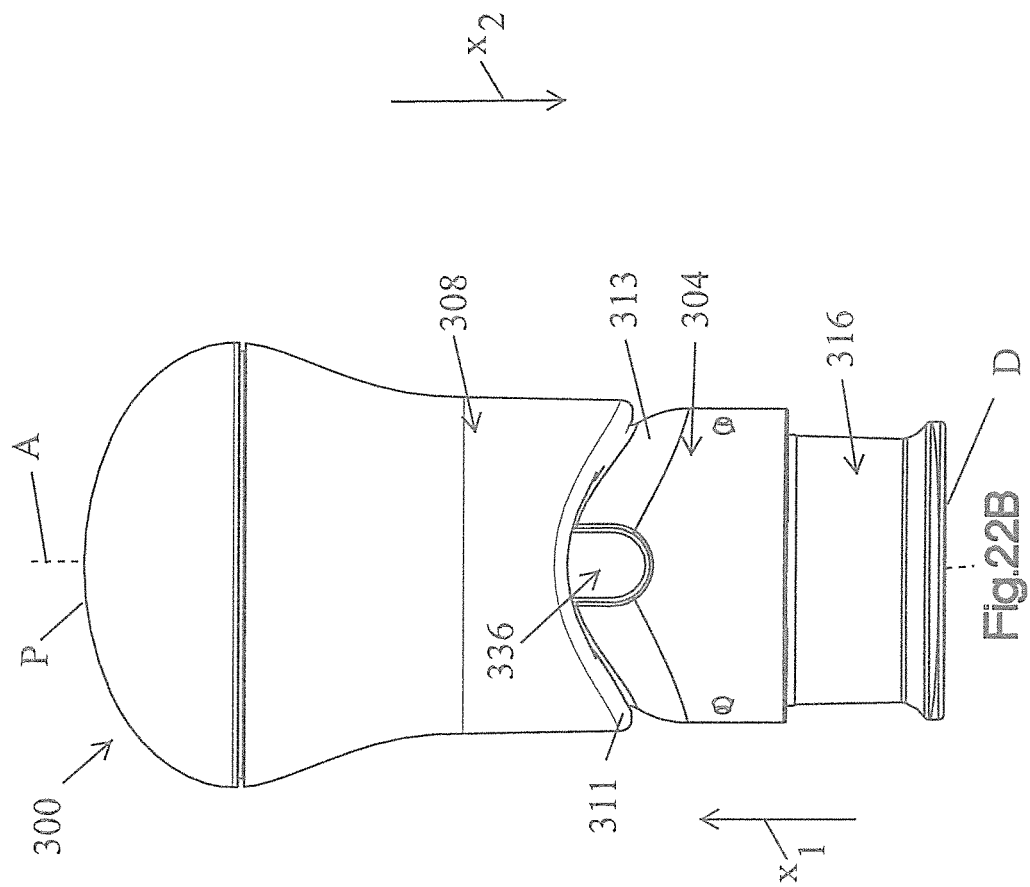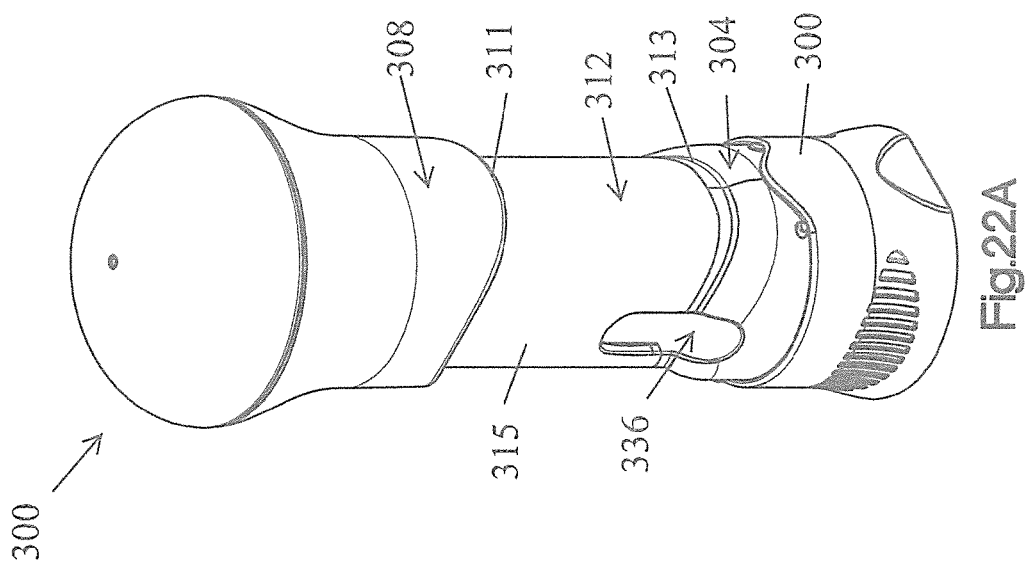

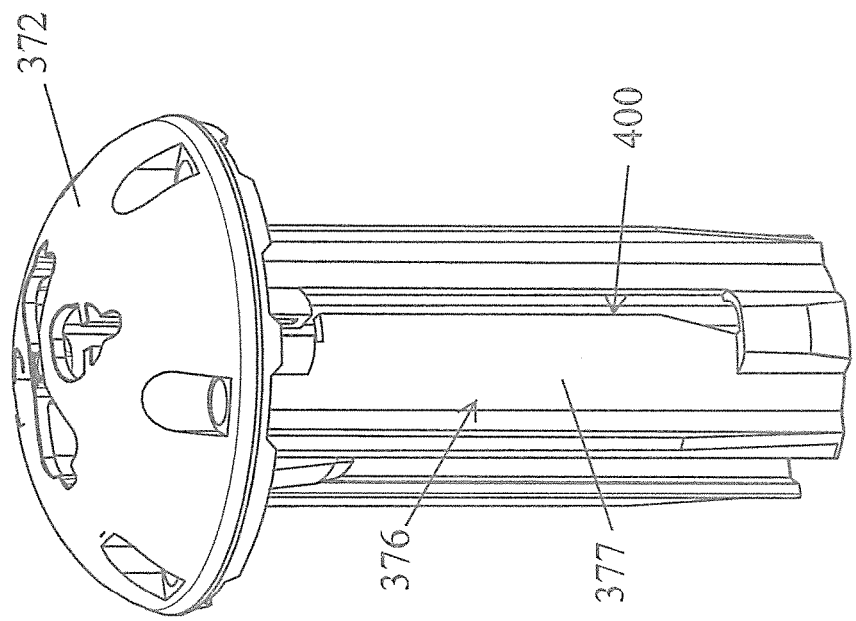
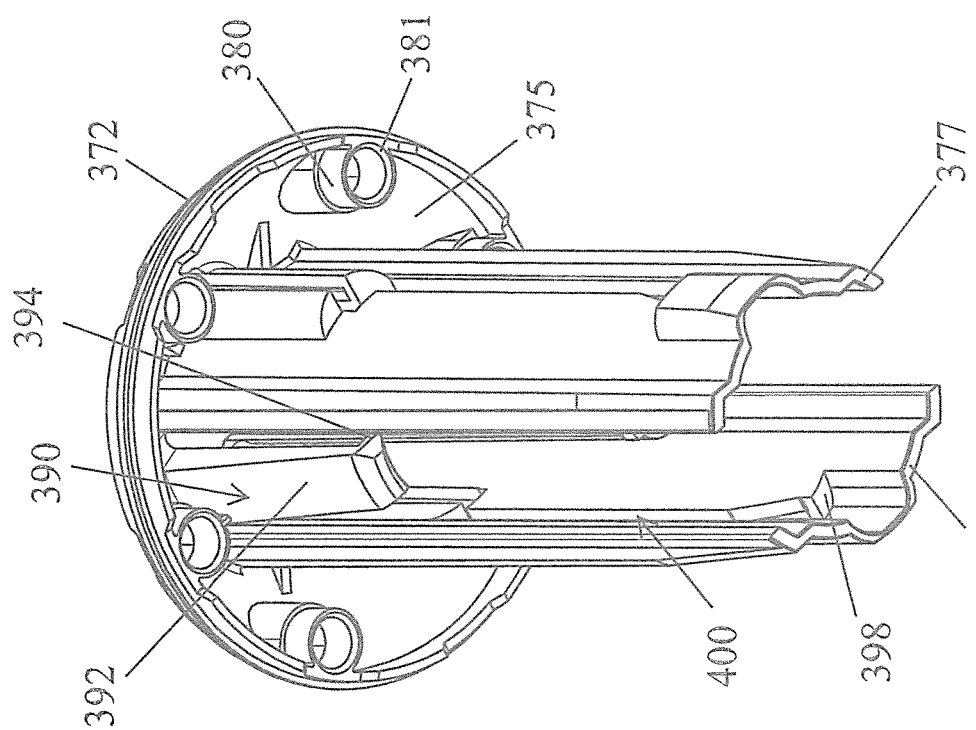

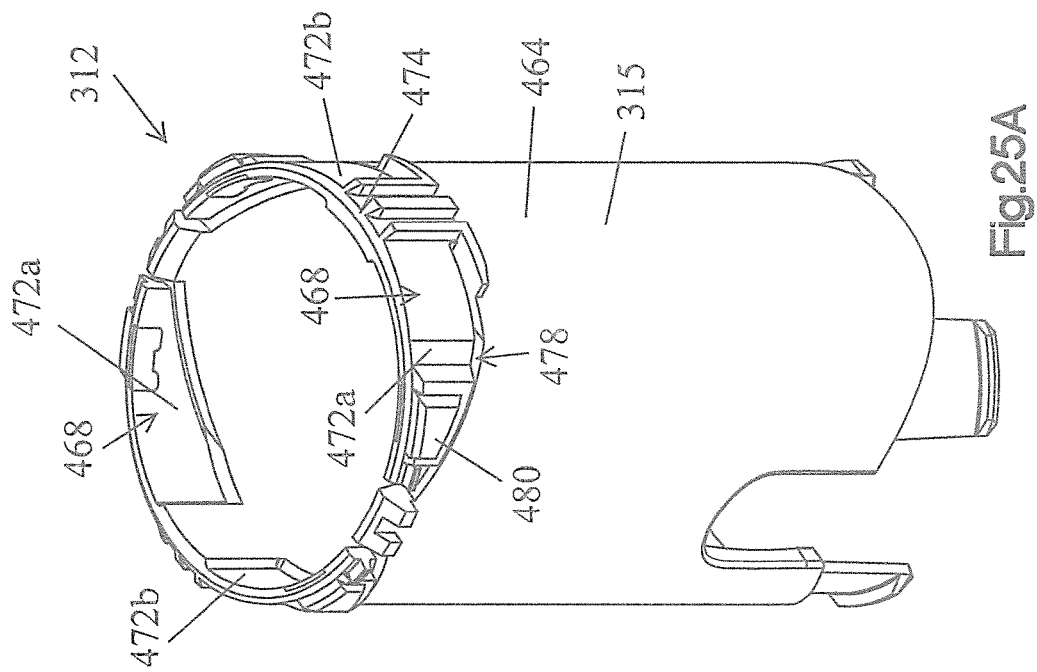
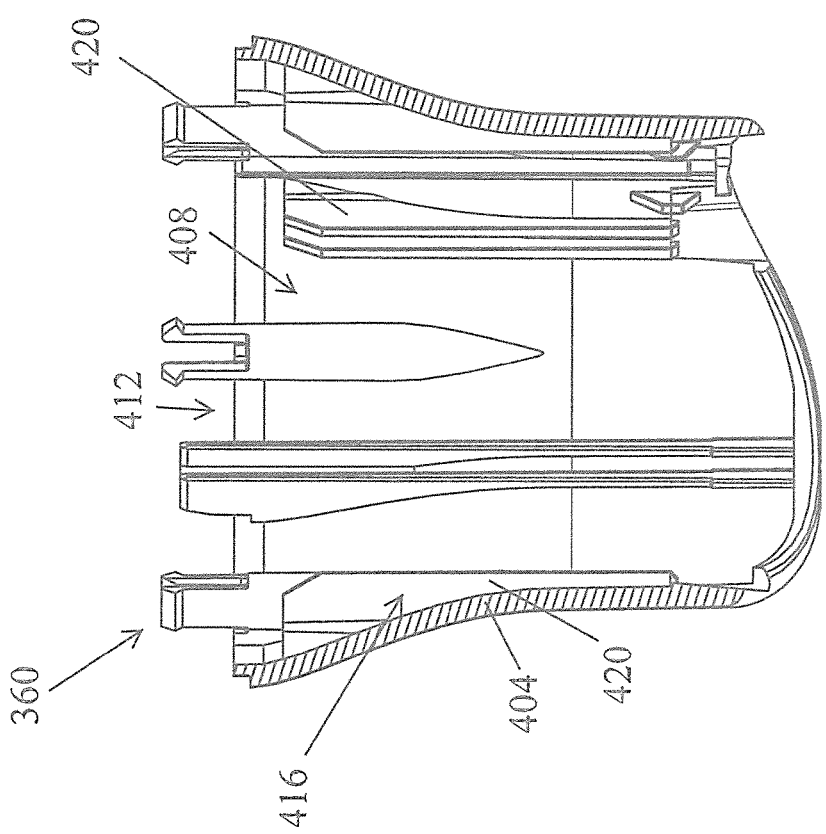

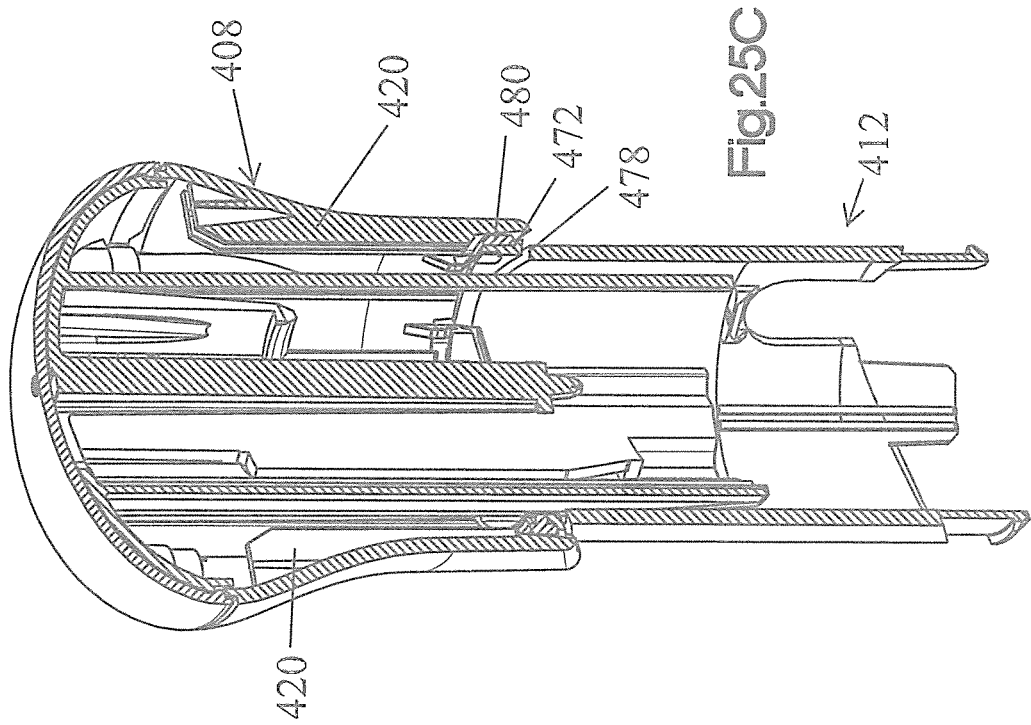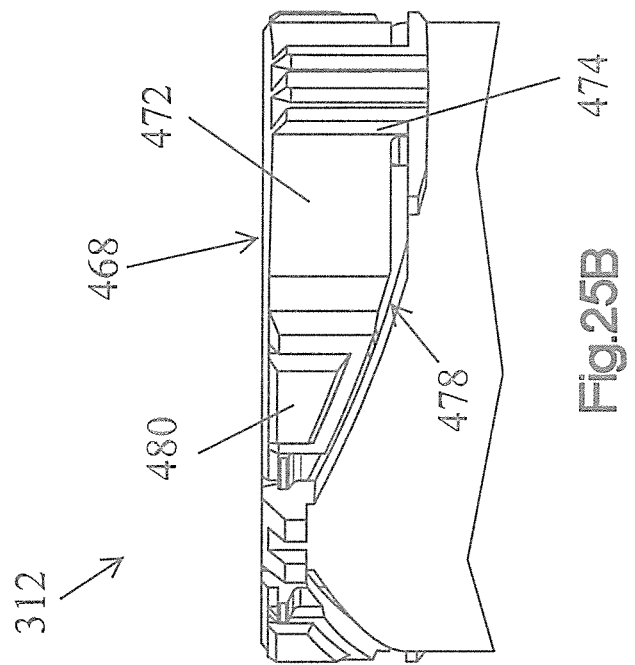

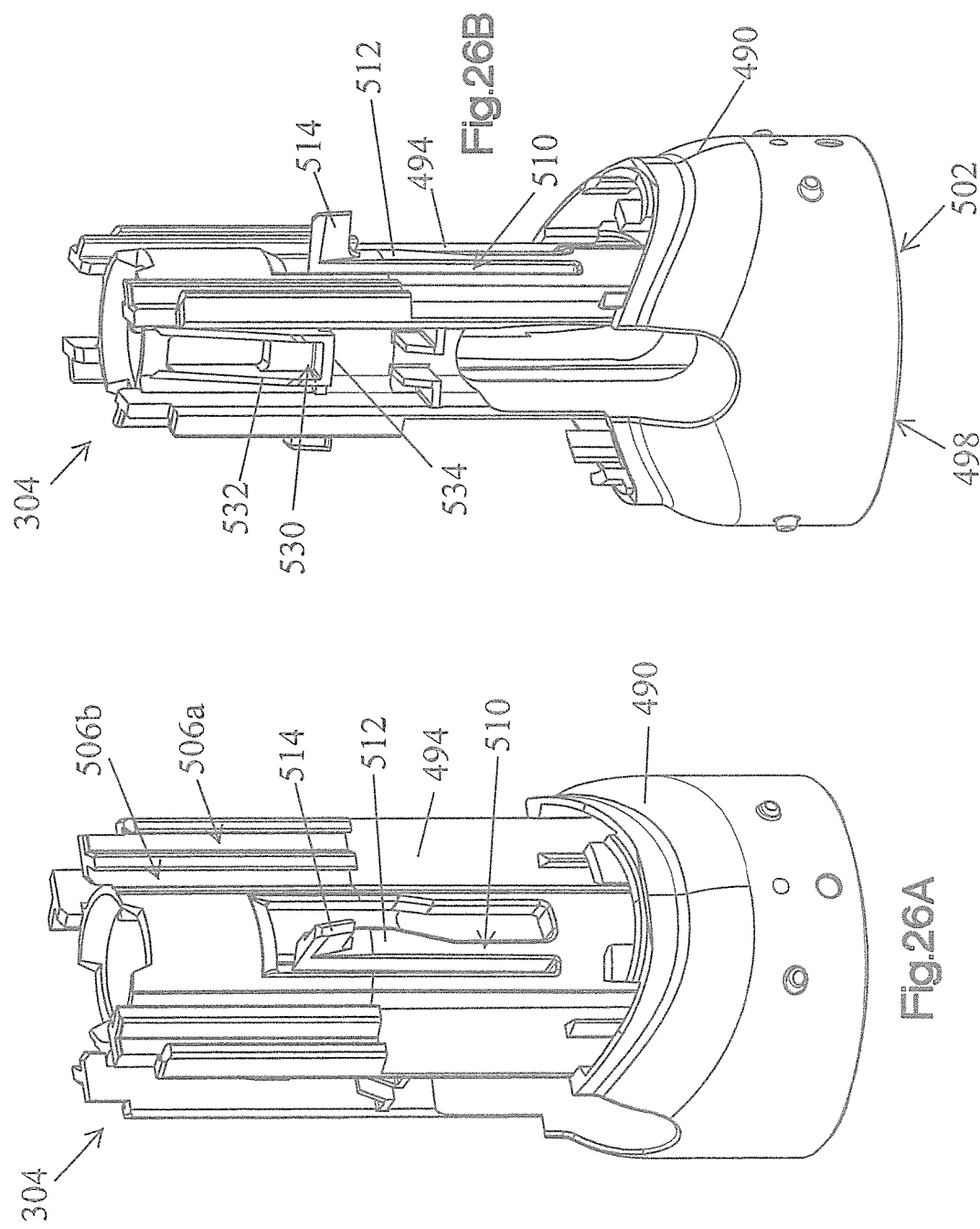

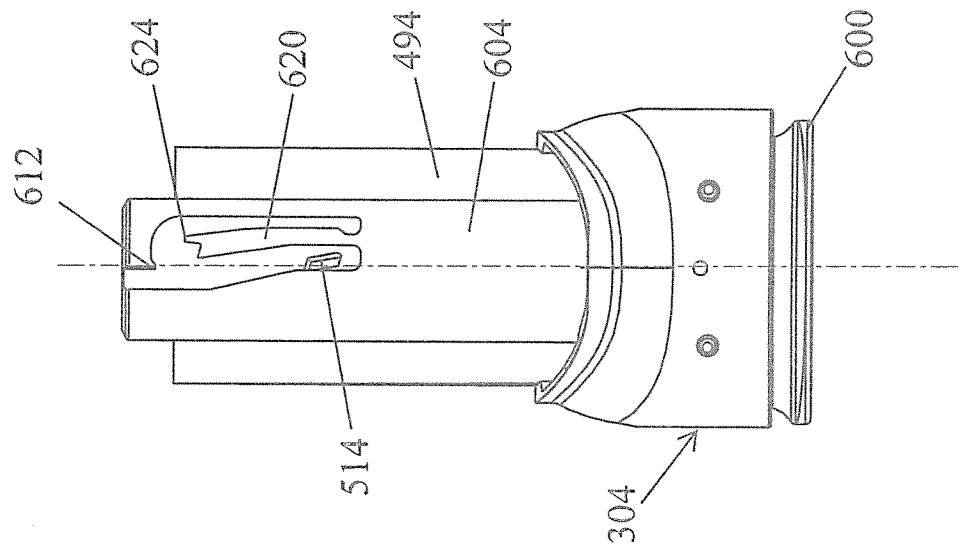
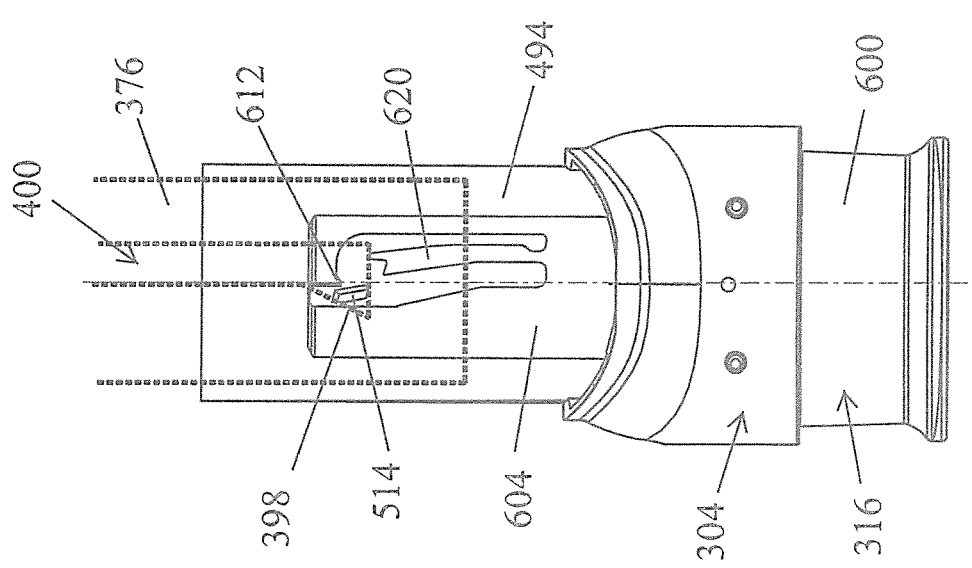

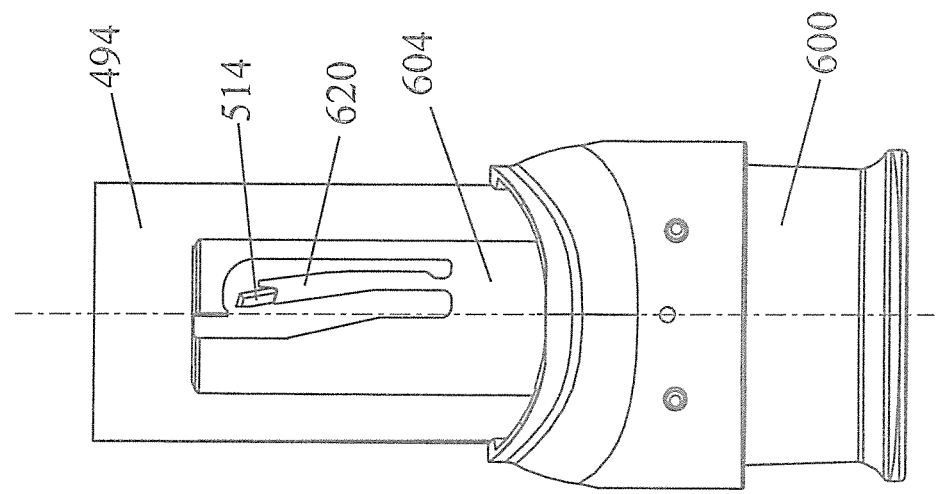
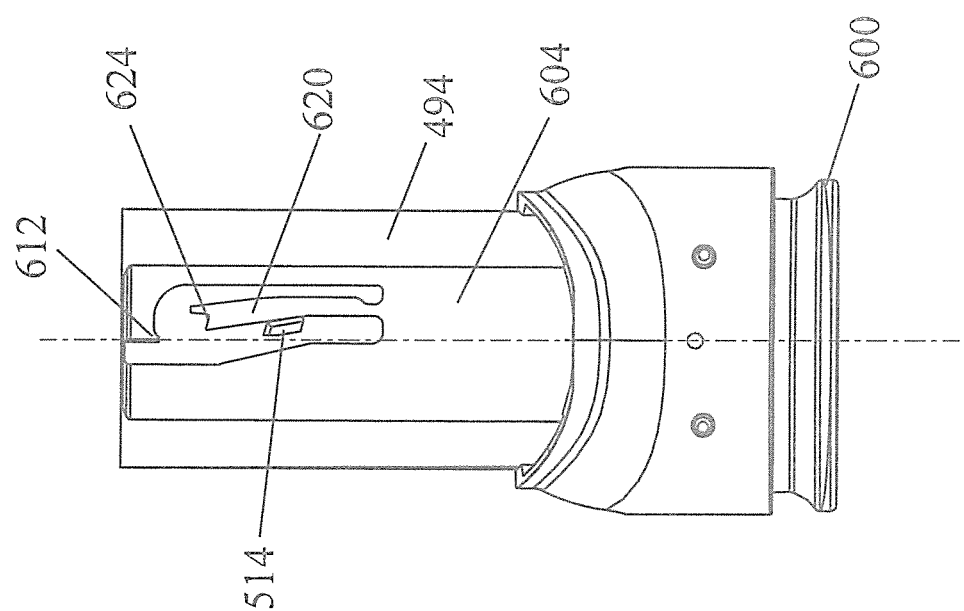

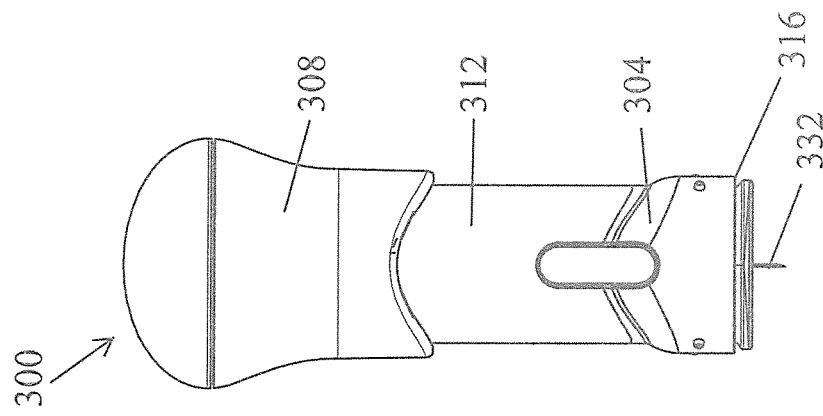
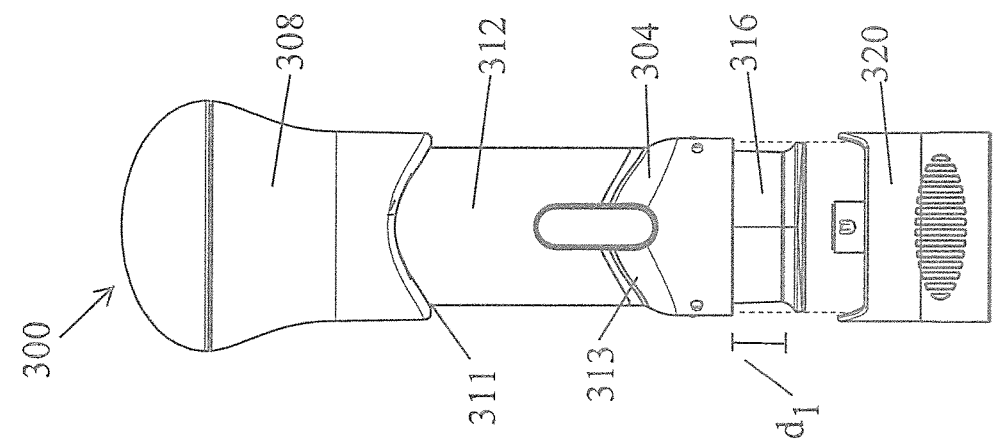
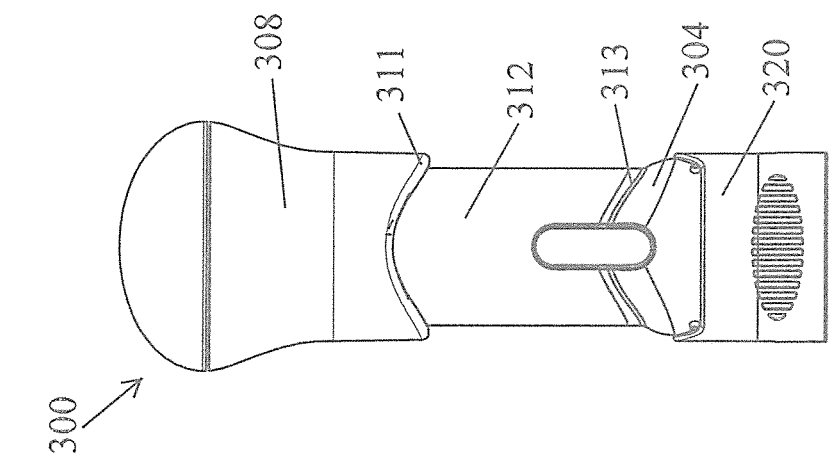

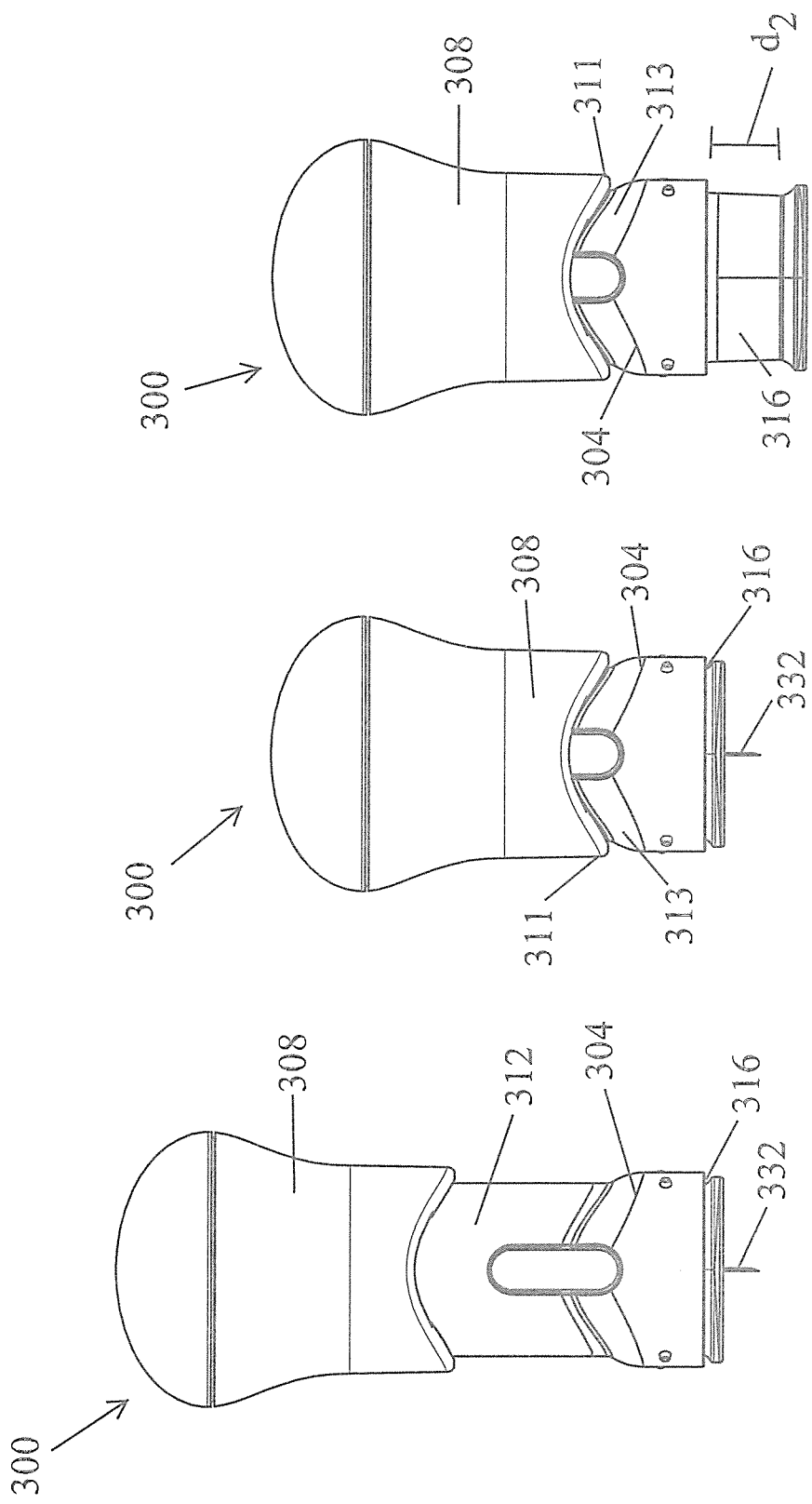

PALM ACTIVATED DRUG DELIVERY DEVICE

CROSS REFERENCE TO RELATED APPLICATIONS

This application is a divisional of U.S. patent application Ser. No. 13/833,978, filed Mar. 15, 2013, which is a continuation-in-part of U.S. patent application Ser. No. 12/905,572, filed Oct. 15, 2010, which claims the benefits U.S. Provisional Application Ser. Nos. 61/361,983, filed on Jul. 7, 2010, and 61/252,378, filed Oct. 16, 2009, the disclosures of all of which are hereby incorporated by reference as if set forth in their entirety herein.

TECHNICAL FIELD

The invention generally relates to methods and devices for parenteral drug delivery. The devices provide for assisted manual drug delivery with confirmation of completion of the drug delivery process. The devices provide a system with improved safety and ease of use and audible, or other forms of, feedback to the user to indicate when drug delivery is in process, completed, or both, to avoid one or both of incomplete dosing and wasted medication as well as to provide a system with improved safety and ease of use.

BACKGROUND

For many years, an accepted method for parenteral drug delivery has been through the use of syringe and needle. The syringe contains a quantity of a drug sold either in a pre-filled syringe or introduced into a syringe by drawing the drug into a syringe from a vial or other container. Syringes have been widely accepted due to their low manufacturing cost and simple, effective design. For the user, however, syringes and needles have a number of drawbacks.

One drawback is that many patients have a fear of needles. In instances in which self-medication is required, such as those requiring multiple, daily injections, patients may not administer their medication according to their prescribed regimen due to the fear of needles, the pain that is often associated with an injection, the dexterity that is required to properly administer a drug via needle and syringe or other, similar factors. For some, that have their vision, dexterity, or awareness impaired, self-administration via needle and syringe may present additional difficulties that can prevent them from receiving their required medication.

There also are safety and disposal concerns associated with needles and syringes not only for the patient, but for those around them that may result from contaminated needles, accidental punctures, cross-contamination, and the like, in addition to the social stigma associated with a needle and syringe drug-treatment regimen. Despite these drawbacks, however, many patients are encouraged to use needles and syringes to deliver their medication due to the ability to control insertion of the needle and the speed of the drug delivery when the plunger in the syringe is depressed and, therefore, control their perception of pain and discomfort associated with this type of drug injection.

Several advances have been made over the years to help facilitate self-administration of medication. Such advances include smaller needles with improved tip-geometry to reduce the pain. Safety syringes that encase the needle before, after, or before and after use have been used to minimize concerns over accidental punctures with needles. Improved ergonomics in syringe design, as well, have been promoted to reduce the dexterity required to accurately and safely self-administer medication via needle and syringe. Pre-filled disposable devices having a form-factor similar to that of a pen were developed to improve dosing accuracy, and auto-injectors have been used to hide the needle from the patient to reduce fears and safety concerns either by retracting the needle or placing a shield around the needle.

While such advances have improved needle and syringe based drug delivery, ergonomic designs, pens, and auto-injectors all retain a substantial similarity to the original needle and syringe concept, thus limiting their acceptance by patients who need to self-administer their medication. Current systems employ a form factor that suggests the common "grab and stab" injection technique, wherein the user grips the device in the palm and places the thumb over an activation button.

Current auto-injectors transfer control of drug delivery into the body to a mechanical system. Because such a system is highly dependent on the specific mechanical design of the auto-injector, patients may require specialized training to use the device and still risk inaccurate dosing. This situation is highly problematic when delivering very expensive drugs that might only be administered on a weekly or even more infrequent basis.

The typical method of use of current auto-injectors includes the patient holding the device against the skin for several seconds while the device is in the process of delivering medication. Many users, and the elderly in particular, may experience fatigue in their arm or hand causing them to exert uneven pressure of the device against the skin, or they may remove the device prematurely. Either situation can result in inaccurate dosing, wasted medication, increased discomfort, and the like. Under any of these circumstances, the current devices and methods that include, or evolved from, the traditional syringe and needle system have shortcomings that compromise the efficacy of a prescribed drug regimen.

Finally, as with any health-care related device or service, the cost of any frequently used component of a treatment regimen must be considered. While providing drugs in vials that are used to fill empty syringes at, or about, the time of a patient's medication may provide the least expensive solution, it adds an additional opportunity for waste or loss of an expensive drug. If that drug requires refrigeration, it may experience degradation each time it is removed and reinserted into the refrigeration device before and after filling the syringe, which can lead to less than expected drug efficacy if the vial contains a quantity of drug that is delivered over a long period of time. While pre-filled syringes offer an advantage in both reliability and convenience, such devices still have the inherent drawbacks previously recited.

With devices such as pre-filled auto-injectors, the device is most commonly manufactured for use with a wide variety of medications, but is tailored to no one medication. Because such devices rely on mechanical systems employing springs to control the injection rate of the drug, many drugs of different viscosity or that require refrigeration and change viscosity appreciably as a result of temperature change, may be delivered too quickly or too slowly for the predetermined spring-force of the auto-injector design. In many instances, too low a spring force may result in incomplete drug delivery, removal of the device before completion of the delivery, or excessive pain and discomfort to the user resulting from a prolonged period during which the injection device is inserted into the body. Too high a spring force, however, can result in drug delivery that is so rapid that it degrades the drug, may result in syringe breakage, or may cause injection force pain to the patient caused by rapid delivery of an acidic drug or by inducing a pressure gradient under the skin or in a vein.

Thus, there are many opportunities for advancement in the field of episodic, parenteral drug delivery that could overcome "needle-phobia", reduce pain to the patient, and increase the safety, reliability and efficacy of many drug treatment regimen.

SUMMARY

In accordance with an embodiment, a device configured to administer a medication can comprise a lower housing that includes a housing latch and a syringe that is supported by the lower housing and is configured to retain a medication. The syringe can have a needle configured to be inserted into tissue. The device can further comprise a needle guard that is movable relative to the lower housing along a first direction from a first position to a second position so as to expose the needle, and an upper housing supported relative to the lower housing. The upper housing can be configured to receive a manual force and move with respect to the lower housing along a second direction opposite the first direction from a pre-use position to a dispensed position in response to the manual force. The device can further comprise a plunger rod carried by the upper housing and movable with the upper housing so as to advance relative to the syringe when the upper housing is moved along the second direction. Advancement of the plunger rod relative to the syringe can cause the syringe to deliver the medication out the needle. The housing latch can releasably interfere with the upper housing when the upper housing is in the pre-use position so as to prevent the upper housing from moving toward the dispensed position, and the movement of the needle guard toward the second position, can cause the interference to be removed, thereby allowing the upper housing to move from the first position to the second position.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 1A is a side elevation view of an embodiment of the present invention.

FIG. 1B is a side view of the embodiment of FIG. 1A after cap removal.

FIG. 1C is a side view of the embodiment of FIG. 1B after depression of the interlock button.

FIG. 1D is a side view of the embodiment of FIG. 1C after the needle guard has been retracted, exposing the needle.

FIG. 11A is a side view of the embodiment of FIG. 10C during drug injection.

FIG. 11B is a side view of the embodiment of FIG. 11A upon completion of drug injection.

FIG. 11C is a side view of the embodiment of FIG. 11B after the needle guard has been extended, concealing the needle.

FIG. 21A is a perspective view of an alternative design of the lower housing of the embodiment of FIG. 10A.

FIG. 21B is a perspective view of an alternative embodiment of the lower housing of FIG. 10A.

FIG. 21C is a cross-sectional view of the lower housing of FIG. 21B.

FIG. 22A is a front perspective view of yet another embodiment of the medication delivery device, in a pre-use position, the medication delivery device including a lower housing, a middle housing attached to the lower housing, an upper housing movably attached to the middle housing from a pre-use position to a dispensed position, and a needle guard movable relative to the lower housing from a first position to a second position and subsequently to a final position.

FIG. 22B is a front elevation view of the medication delivery device shown in FIG. 22A in a post-use position with the upper housing substantially covering the middle housing.

FIG. 24A is a bottom perspective view of the upper housing body shown in FIG. 23, the upper housing body including a pair of guides that each defines an abutment surface and a guide channel.

FIG. 24B is a side elevation view of the upper housing body shown in FIG. 24A.

FIG. 24C is a cross-sectional view of the skirt shown in FIG. 23, the skirt including a body and four friction members defined as rails that extend from the body.

FIG. 25A is a perspective view of the middle housing shown in FIG. 23, the middle housing including a sidewall and four friction members defined by cantilevered portions that extend from the sidewall.

FIG. 25B is an enhanced side elevation view of one of the cantilevered portions of the middle housing shown in FIG. 25A.

FIG. 25C is a cross-sectional view of the medication delivery device shown in FIG. 22A showing the ribs of the skirt interfering with the cantilevered portions of the middle housing when the upper housing is moved along the middle housing from the pre-use position to the dispensed position.

FIG. 26A is a perspective view of the lower housing shown in FIG. 23, the lower housing including a pair of housing latches that are configured to interfere with the guides of the upper housing to maintain the upper housing in the pre-use position and are also configured to interfere with the needle guard to maintain the needle guard in the final position so as to prevent reuse of the device.

FIG. 26B is a front perspective view of the lower housing shown in FIG. 26A.

FIG. 29A a partial front elevation view of the medication delivery device shown in FIG. 22A when the upper housing is in the pre-use position and the needle guard is in the first position such that stops of the needle guard extensions abut the housing latches and maintain the housing latches in interference with the abutment surfaces of the upper housing guides so as to maintain the upper housing in the pre-use position.

FIG. 29B is a partial front elevation view of the medication delivery device shown in FIG. 29A with the upper housing guide removed for clarity when the needle guard has moved to the second position such that the stops of the needle guard extensions no longer abut the housing latches.

FIG. 29E is a partial front elevation view of the medication delivery device shown in FIG. 29D with the upper housing guide removed for clarity when the upper housing is in the dispensed position and the needle guard begins to move from the second position and toward the final position.

FIG. 29F is a partial front elevation view of the medication delivery device shown in FIG. 29E when the needle guard is in the final position and the needle guard latches are in interference with the housing latches to thereby lock the needle guard in the final position.

FIG. 30A is a front elevation view of the medication delivery device shown in FIG. 22A in a pre-use position.

FIG. 30B is a front elevation view of the medication delivery device shown in FIG. 30A with the cap removed so as expose the needle guard.

FIG. 30C is a front elevation view of the medication delivery device shown in FIG. 30B with the needle guard in the second position.

FIG. 30D is a front elevation view of the medication delivery device shown in FIG. 30C with the upper housing moving toward the dispensed position.

FIG. 30E is a front elevation view of the medication delivery device shown in FIG. 30D with the upper housing in the dispensed position.

FIG. 30F is a front elevation view of the medication delivery device shown in FIG. 30E with the needle guard in the final position.

DETAILED DESCRIPTION OF ILLUSTRATIVE EMBODIMENTS

The following detailed description is to be read with reference to the drawings in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention.

The present invention is a drug delivery device, and methods for its use, which device overcomes many of the limitations and drawbacks of conventional syringes and needles as well as auto-injector-type devices. To overcome the drawbacks and limitations of prior devices and to address the unfilled needs in the art, embodiments of the presently disclosed device and methods include a device that is configured such that the user does not see and cannot touch the needle, reducing needle-phobia and potential for needle contamination. This includes automatic shielding of the needle after delivery of the drug.

Embodiments of the device have an ergonomic form-factor that permits operation one handedly and conveniently allows for alternate site injections, such as the leg, arm, or abdomen. In embodiments that include a pressure-sensitive triggering, a needle guard latch inhibits movement of the needle. In this manner, the device includes a safety mechanism that will not allow the needle to be exposed if it is not pressed against the injection site.

In FIGS. 1A-1D is illustrated one embodiment of the device of the invention that includes a window 104 to view the drug prior to use. A colored indicator may appear in the window after the device has been used, to provide a visual indication to the user of whether the device's drug has been spent. Further, after the drug is delivered, increased safety and reduction in the possibility of accidental needle punctures is provided.

Figure 4:
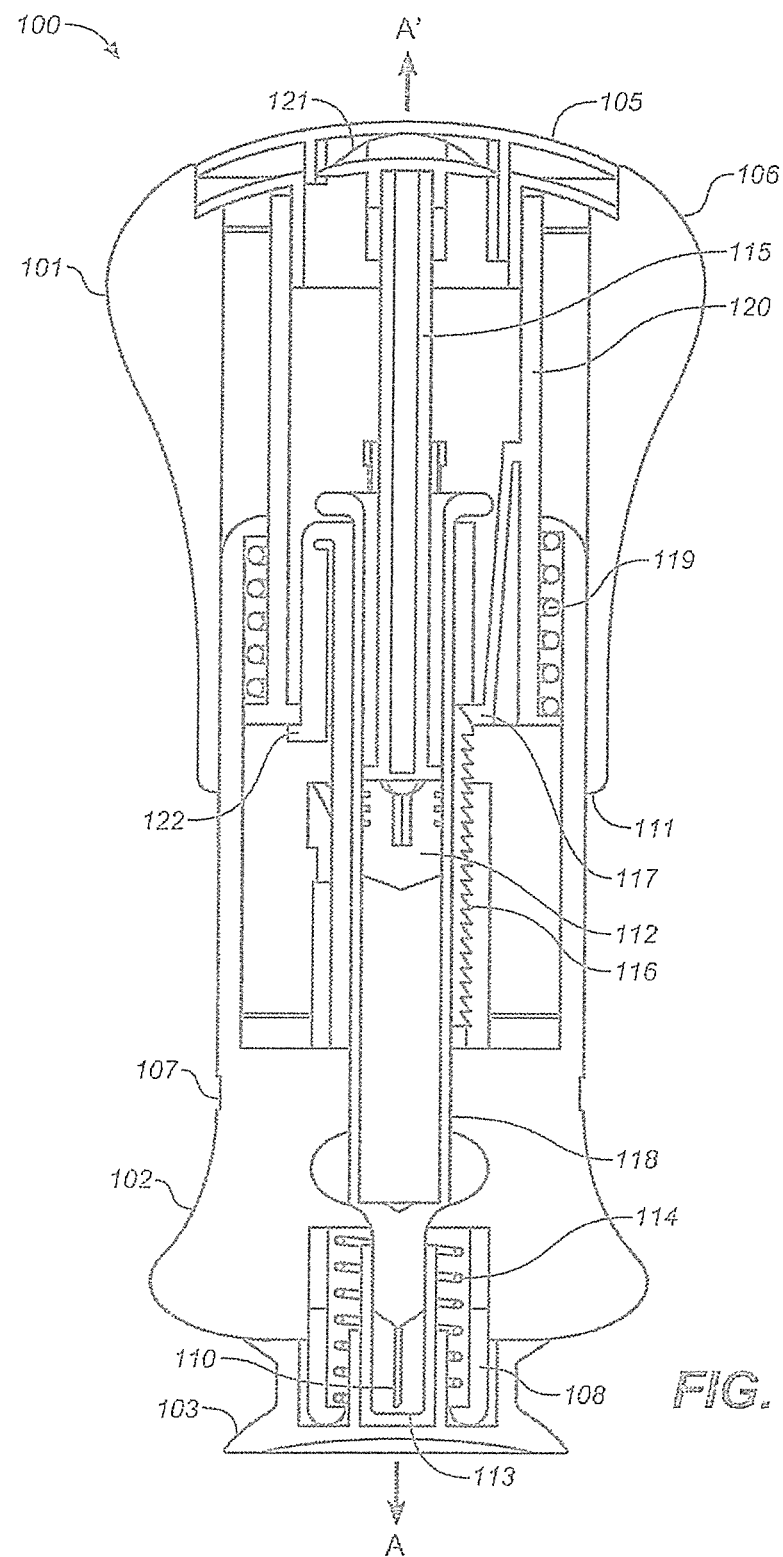
FIG. 4 is a depiction of a cross-sectional view of the embodiment of FIG. 1A.
Figure 5:
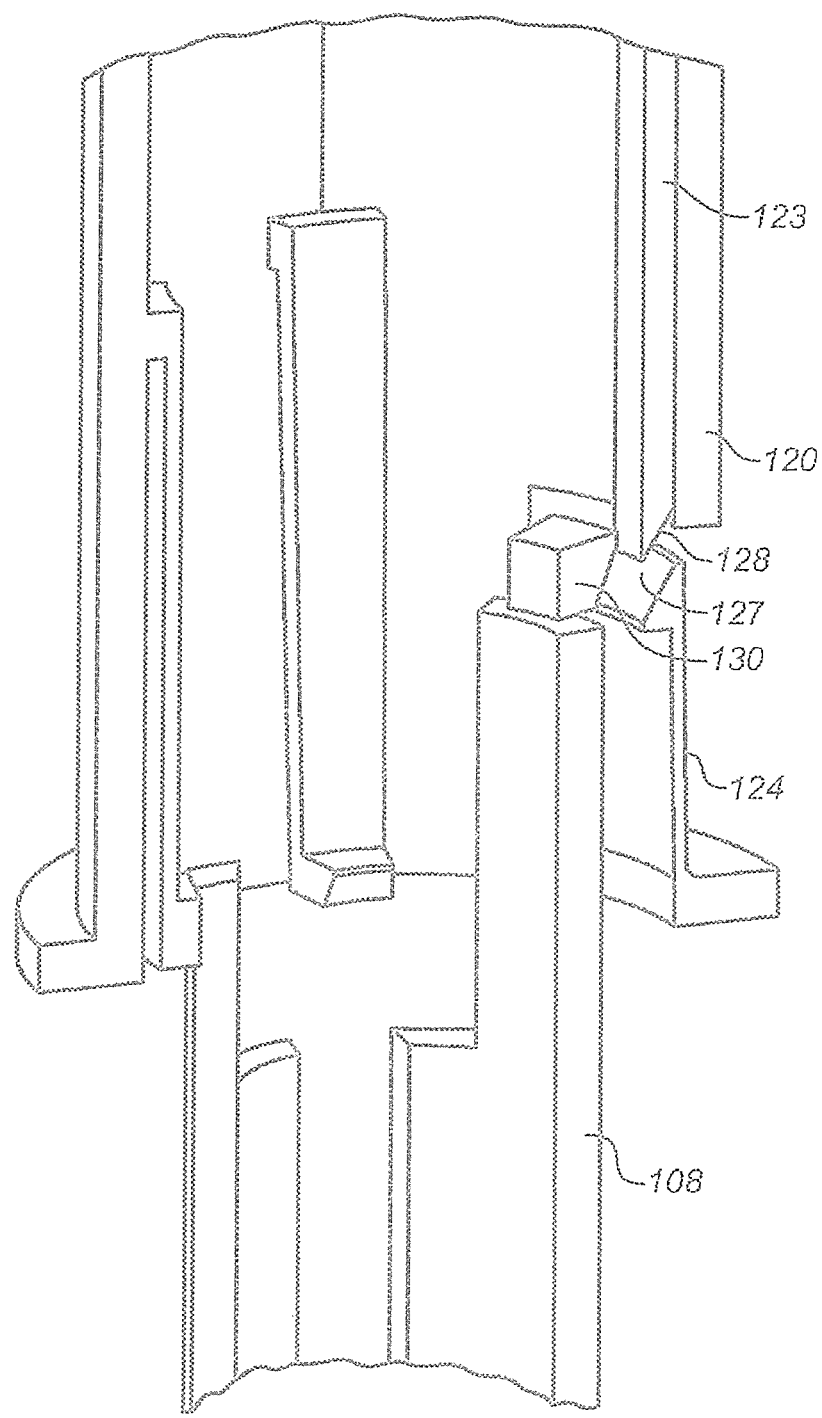
FIG. 5 is a depiction of a partial cross-sectional view of a portion of the embodiment of FIG. 1A, depicting a latch.
Figure 7:
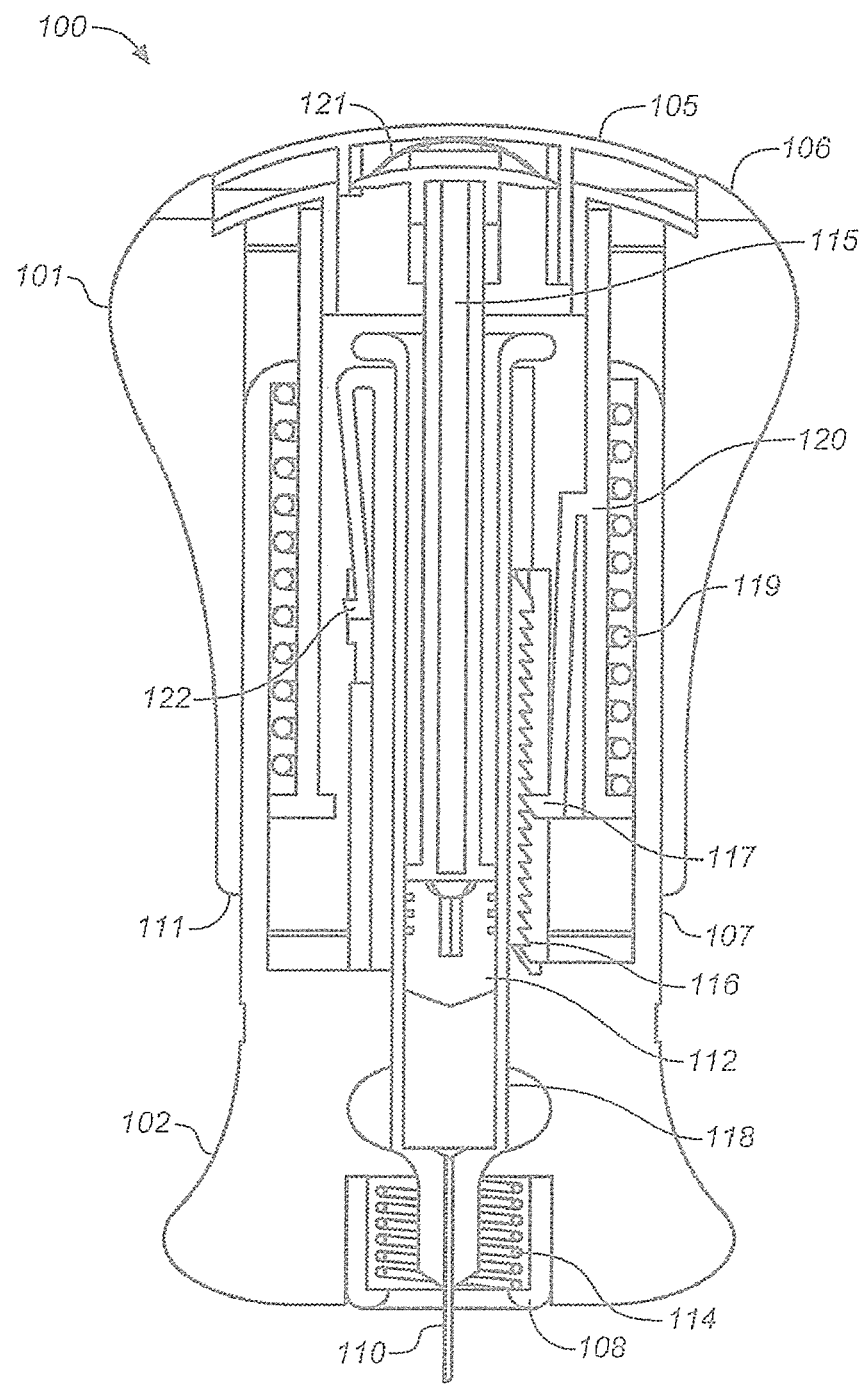
FIG. 7 is a depiction of a cross-sectional view of the embodiment of FIG. 2A.

To ensure that the user is aware of the status of the drug delivery and whether it is completed, this embodiment of the invention includes pawls and ratchets, such as those illustrated by the pawl 117 and ratchet 116 shown in FIGS. 4 and 7, that engage to produce one or more audible clicks when the injection is completed. Such a mechanism may signal the user that the dose has been delivered and the device can be removed from the skin, preventing premature withdrawal of the device from the injection site. Thus, the user actively participates during the entire delivery process, unlike conventional auto-injectors for which the user may need to wait several seconds for an assurance that the full dose has been administered.

To provide greater feedback to the user, the disclosed system of pawls and ratchets also provides audible clicks and motion of the device during delivery to indicate that the injection is progressing. In yet another embodiment, a louder click at the end of delivery alone or in combination with a visual indicator provides 1 feedback confirming that the delivery is completed.

Moreover, the present invention has a friendly, unintimidating design and method of operation, unlike conventional needle safety devices and auto-injectors, which are reminiscent of syringes and discomforting to the user. Additionally, unlike conventional auto-injectors, the user controls insertion of the needle and injection of the drug as described hereinafter.

In FIGS. 1 through 9 are shown an exemplary device of the invention. In FIGS. 1A through 1D is shown an embodiment of the device in various stages leading up to injection of the drug and in FIGS. 2A through 2C is shown the embodiment during and after injection of the drug. FIG. 1A shows the device 100 in its pre-use configuration as it may be received by the user. In this relaxed position, upper housing 101 partially overlies the proximal or uppermost portion of lower housing 102. In describing the various embodiments of the device, the term proximal is used in relation to the upper end of the device and distal is used in relation to the bottom surface of the device. For example, in FIG. 1B, distal is used in relation to bottom surface or bottom 131 of device 100.

Figure 3:
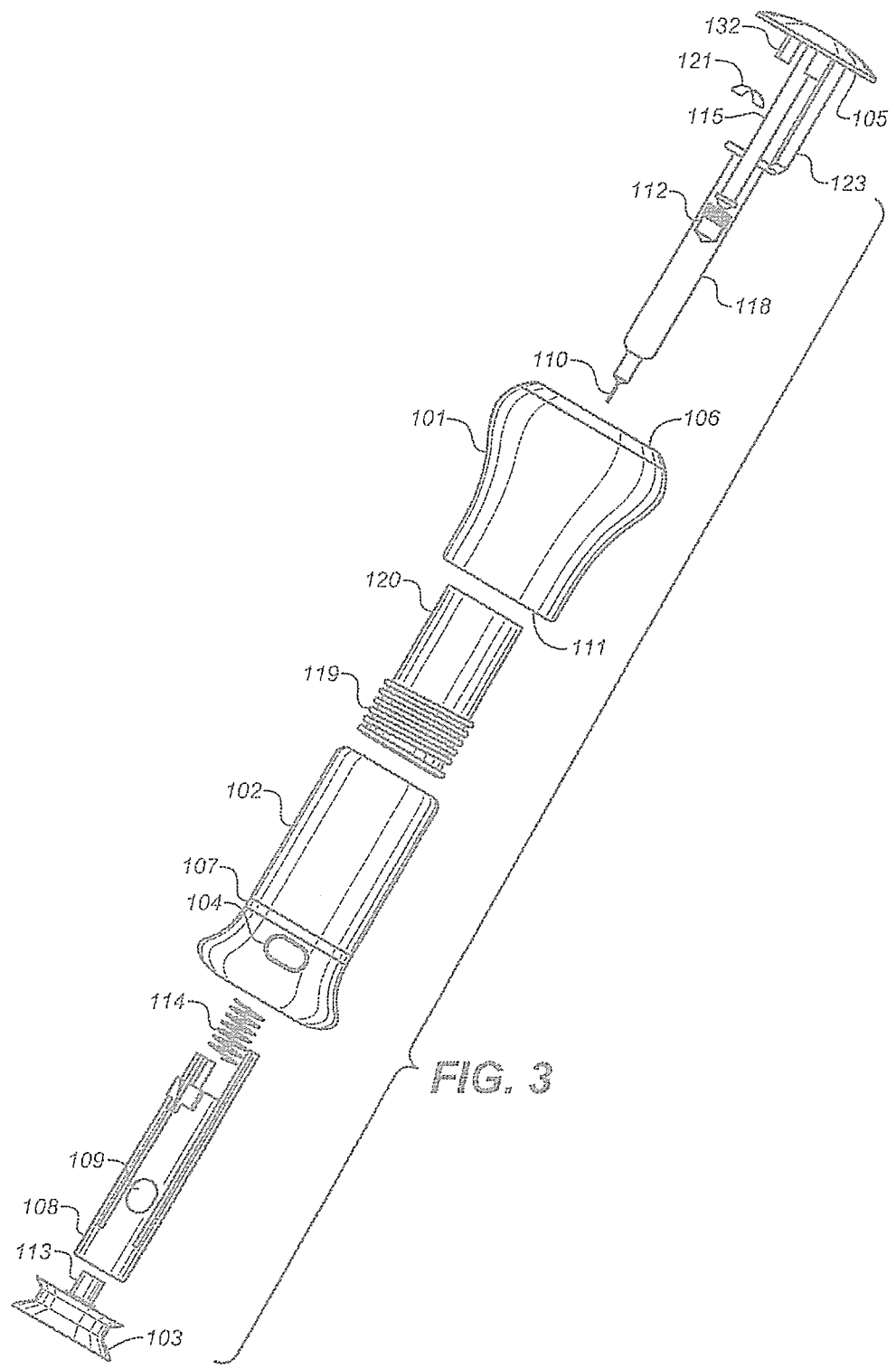
FIG. 3 is a depiction of an exploded view of the embodiment of FIG. 1A.

As shown, the device's outwardly visible features include upper housing 101, lower housing 102, cap 103, window 104, interlock button 105, grip ring 106, bottom edge 111 of the upper housing 101 and dose indicator 107. FIG. 3 is an exploded view of the components of this embodiment of the invention.

A preliminary step in using the device is to remove cap 103, which is removably attached to lower housing 102, as shown in FIG. 1B. Removing the cap 103 simultaneously removes needle shield 113 and exposes needle guard 108. Window 104 and needle guard slot 109, each of which are preferably present on both sides of the device, allow the user to view and inspect an internally housed syringe 118 and its drug contents.

In use, the device is grasped by placing the palm of the hand over the top of the upper housing 101, similar to how one grasps a floor-mounted, automotive gear shift. Grip ring 106 provides a visual cue to the user on how to grasp the device. In one embodiment, grip ring 106 is covered, or coated, or made of a suitable elastomeric material including, without limitation, neoprene rubber, urethane, polyurethane, silicone, natural rubber, thermoplastic elastomer ("TPE"), or combinations thereof to provide a non-slip and comfortable gripping surface.

The user presses the device, by downward pressure of the palm on grip ring 106 and interlock button 105, against the body at the desired injection location, typically the top or side of the upper leg, the abdomen, or the side or back of the upper arm. The pressure of the palm on interlock button 105 causes it to deflect downwardly, as shown in FIG. 1C, which in turn unlatches needle guard latch 124, shown in FIG. 5, allowing the needle guard 108 to slide upwardly, and exposing needle 110 (note that some device components have been removed from FIG. 5 for illustration purposes). Needle guard latch 124 is formed integrally with a portion of the distal end of upper housing sleeve 120. Upper housing sleeve 120 is a hollow cylinder a portion of which resides in the upper housing 101 and portion of which resides in lower housing 102 when the device is in the relaxed position. Upper housing sleeve 120 is fixedly attached to upper housing 101 and performs latching functions and acts to trap biasing element 119 against lower housing 102 as described in more detail below.

Needle guard latch 124 includes inwardly, with respect to the longitudinal center axis A-A' of the device, ramped surface 127 and stop 130 at its uppermost end. To unlatch the needle guard latch 124, an outwardly ramped surface 128, complementary to surface 127, that forms the distal end of interlock button extension 123, engages ramped surface 127 on the needle guard latch 124. Engagement of surfaces 127 and 128 causes the needle guard latch 124 to deflect outwardly, with respect to the center axis, removing stop 130 from blocking the upward movement of needle guard 108. The latching mechanism and needle guard 108 are preferably configured so upward movement of needle guard 108 is prevented unless the interlock button 105 is fully depressed. This protects the needle from contamination and damage due to contact with other surfaces, protects the user from accidental needle punctures, and shields the needle from view.

As the user continues to press downwardly on upper housing 101, needle guard 108 moves upwardly, exposing and allowing needle 110 to penetrate the user's skin, stopping when bottom surface 131 of the lower housing 102 is substantially flush against the skin. Once needle guard 108 passes beyond stop 130, the user may release interlock button 105, or chose not to, without affecting the remaining injection steps. When interlock button 105 is released, resilient member 121, returns interlock button 105 to the up position. Movement guide 132 acts to ensure that interlock button travels straight up and down.

The needle insertion process described herein gives control of insertion to the user. This feature allows the user to take advantage of a commonly used method often employed by insulin-dependent diabetics: if the needle is brought into contact with the skin and held there without piercing the skin, after a few seconds the user will no longer feel the presence of the needle, at which point the needle can be inserted pain free by increasing the pressure applied to the needle.

Figure 2A:
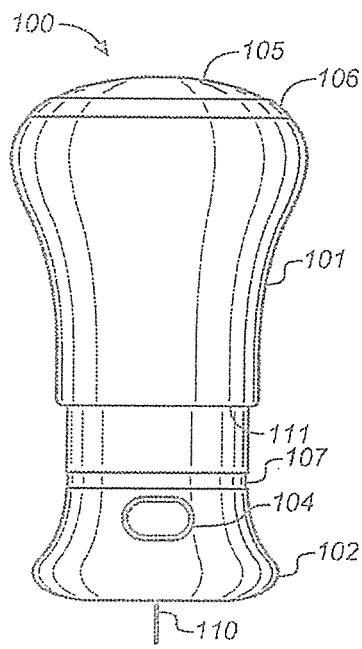
FIG. 2A is a side view of the embodiment of FIG. 1D during drug injection.
Figure 2B:
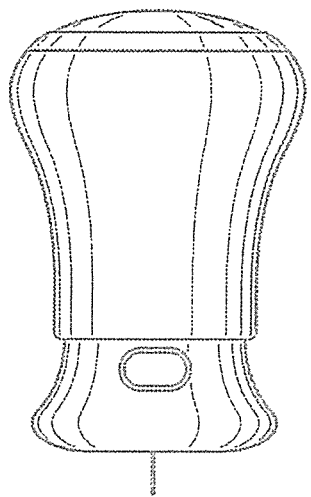
FIG. 2B is a side view of the embodiment of FIG. 2A upon completion of drug injection.
Figure 2C:
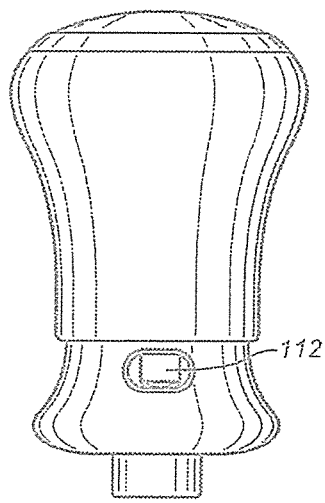
FIG. 2C is a side view of the embodiment of FIG. 2B after the needle guard has been extended, concealing the needle.
Figure 6:
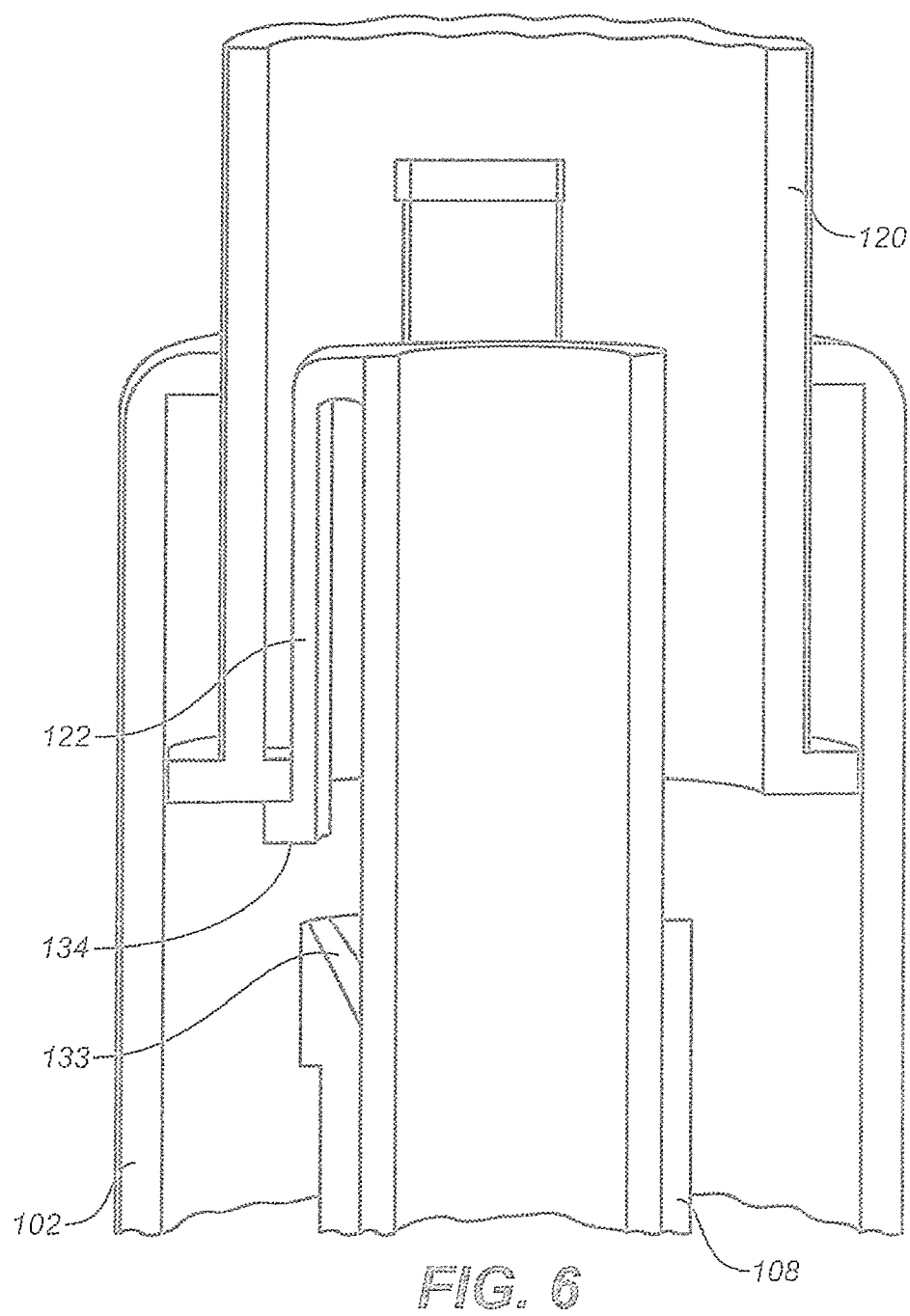
FIG. 6 is a depiction of a partial cross-sectional view of a portion of the embodiment of FIG. 1A, depicting a latch.

After needle 110 has been inserted into the user, the injection process typically begins, as shown in FIGS. 2A through 2C. With reference to FIG. 6, aA housing latch 122 that is a part of lower housing 102 is shown in close-up detail and prevents the upper housing 101 from moving with respect to the lower housing 102 in the device's pre-use state (note that some device components have been removed from FIG. 6 for illustration purposes). When needle guard 108 has completed its upward travel, ramped surface 133 on needle guard 108 contacts a ramped portion of surface 134 that forms the end of housing latch 122, causing the housing latch 122 to deflect inwardly, thus allowing the upper housing 101 and upper housing sleeve 120 to move downwardly.

After inserting needle 110 into the body, the user maintains pressure on the upper housing 101. As shown in FIGS. 3, 4, 7 and 8 a plunger rod 115 pushes on a plunger 112. Plunger rod 115 is connected fixedly to the upper housing 101 and syringe 118 is secured to or held in a cylinder formed within lower housing 102. Thus, when the upper housing 101 moves downwardly with respect to and over the lower housing 102, a drug inside the syringe 110 is delivered through the needle 110 to the patient by the downward movement of plunger rod 115 and plunger 112 within syringe 118.

After the housing latch 122 is disengaged, a biasing element 119 that surrounds the distal end of upper housing sleeve 120, is freed from a tensioned state to apply a downward force on the upper housing 101 by exerting a downward force on upper housing sleeve 120, which is fixedly attached, at its uppermost end, to upper housing 101. Biasing element 119 also can be used to provide energy for assisting with advancement of plunger rod 115 and plunger 112 with the user providing additional required force resulting in injection of the drug or the energy supplied by the biasing element 119 may be sufficient only to advance plunger rod 15 and plunger 112. In another embodiment of the present invention, biasing element 119 provides sufficient force to inject the drug, without additional force input required by the user, thus providing an injection device in which the needle is manually inserted and the drug is automatically injected. The biasing element may be any component capable of exerting a downward force on upper housing sleeve 120 to the degree desired and may be, without limitation, a spring, a compressed gas actuator, a hydraulic drive, a wax actuator, an electrochemical actuator, a shape memory alloy, and the like and the combinations thereof. In the embodiment depicted in FIGS. 1 through 9, the user provides the additional force required to advance the plunger rod 115 and plunger 112 by pressing downwardly on the upper housing 101. Thus, the force required by the user to inject the drug is reduced, in a manner analogous to the way power steering in a car reduces the force required by the driver to turn the steering wheel. Unlike conventional auto-injectors, the user contributes to the force required for injection and the present invention provide the user control over the rate of injection of the drug.

Referring to FIGS. 4 and 7, cross sectional views of embodiments of the present invention are shown both before and after delivery of the drug has commenced, respectively. As the drug is being delivered, a pawl 117 which is attached to upper housing sleeve 120 moves along a ratchet 116 that is attached to the lower housing 102. The pawl 117 and the ratchet 116 may serve, at least, the following two functions.

First, separation of upper housing 101 from lower housing 102 by pulling them apart is prevented. Second, the motion of pawl 117 along ratchet 116 produces a soft clicking noise, providing feedback to the user that upper housing 101 is moving and the drug is being delivered. Additionally, and as illustrated in FIG. 8, at the end of travel of upper housing 101, pawl 117 may be configured to engage a deeper recess in ratchet 116, thereby producing a louder clicking sound, which can provide an audible signal to the user that end of travel has been reached and the drug has been fully delivered, and further locking the upper housing 101 in place to prevent resetting or reuse of the device.

Figure 8:
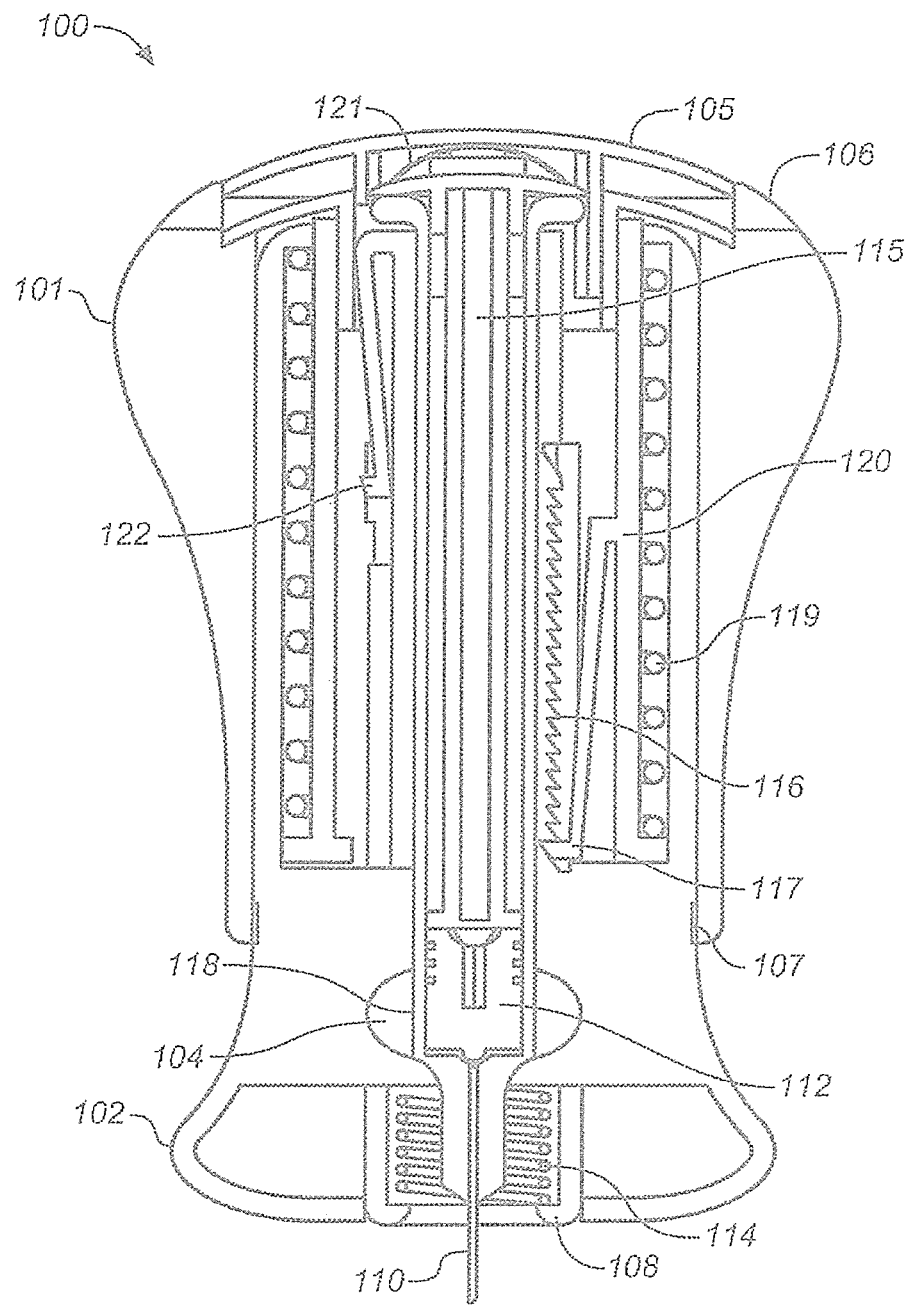
FIG. 8 is a depiction of a cross-sectional view of the embodiment of FIG. 2B.

Referring to FIGS. 2B and 8, when the drug is completely injected and upper housing 101 is at the end of its travel, bottom edge 111 of upper housing 101 covers dose indicator 107. Dose indicator 107 is a circumferential, colored ring at the distal portion of lower housing 102. This provides a visual cue to the user that the drug delivery has been completed.

Prior to use, the patient can view the drug through window 104 to inspect it for clarity and particulates. After use, the plunger 112 can be viewed in the window 104, indicating that the device has been used. Alternatively, the window can be designed such that the plunger rod 115 as well is visible after the injection is complete. The plunger 112 and the plunger rod 115 can be brightly colored to provide a clear indication to the patient that the device has been used.

Figure 9:
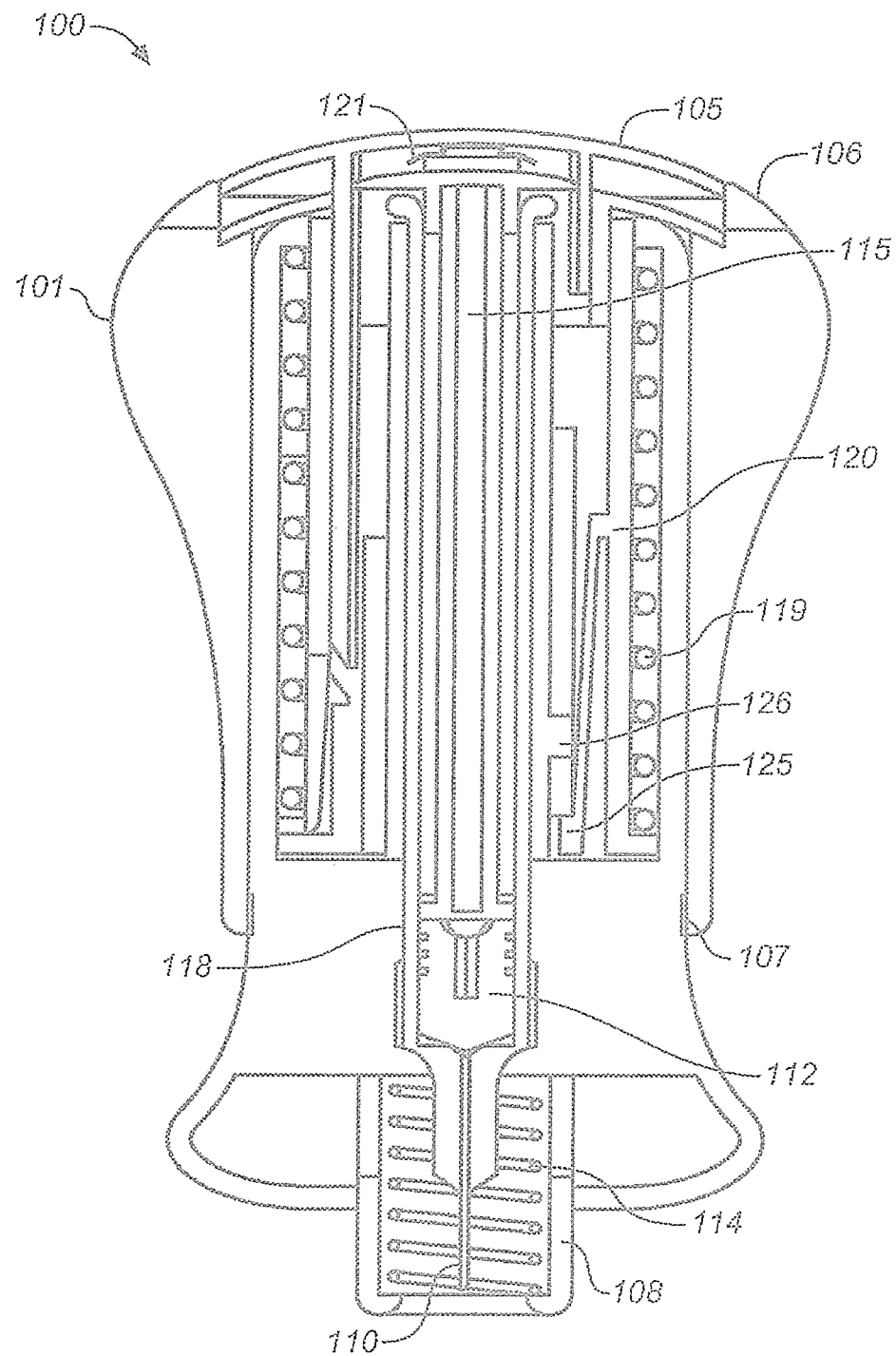
FIG. 9 is a depiction of a cross-sectional view of the embodiment of FIG. 2C

Referring to FIGS. 2C and 9, after completing the injection, the user removes device 100 from the skin, and needle guard return element 114 causes needle guard 108 to extend over needle 110, protecting the user and others from accidental needle punctures. Needle guard return may be any element capable of causing needle guard 108 to extend over needle 110 including, without limitation, a spring, a compressed gas actuator, a hydraulic drive, a wax actuator, an electrochemical actuator, a shape memory alloy, and the like and the combinations thereof. Once needle guard 108 is fully extended, a needle guard lock 125 engages a slot in needle guard 108, preventing the needle guard 108 from retracting. Needle guard lock 125 is a cantilever latch extending inwardly from the inner surface of upper housing sleeve 120. Lower housing rib 126, a part of the lower housing 102, may be configured to prevent the needle guard lock 125 from engaging the slot in the needle guard 108 prematurely during delivery by blocking the slot. In another embodiment of the present invention, needle guard 108 may extend and lock in place if device 100 is removed before delivery is complete, to prevent reuse, or sharing of the device.

With the assisted delivery approach offered by the present invention, the user is actively engaged during the entire delivery process. This is distinguishable from the activation process for conventional auto-inserters, in which after pressing the button, the user passively waits, for several second, for the drug to be delivered, sometimes wondering whether the injection is in process or not.

The assisted activation approach of the present invention has the additional advantage that it reduces development time and cost associated with modifying the injection device for delivering different drugs because the user controls delivery speed by varying the force applied to the upper housing 101. If the plunger is slightly stuck, the user can apply a little more force, unlike conventional auto-injectors that must be designed for worst case force requirements, that vary depending on the drug, cartridge, plunger, needle, and friction in the mechanism.

In another embodiment, the interlock button 105 and the interlock spring 121 can be omitted from the design. In this embodiment, the upper housing 101 is free to move downwardly before hitting a stop. This movement is used to unlock the needle guard 108 using a mechanism similar the interlock mechanism described above, allowing the needle guard 108 to retract. Once the needle guard 108 is fully retracted, it may disengage another latch that allows the upper housing 101 to discontinue moving downwardly and inject the drug in a similar manner as is described above.

In FIGS. 10 through 18 is depicted yet another embodiment of the invention. In FIG. 10A is shown device 200 with upper housing 205, lower housing 202 and middle housing 201 therebetween. Upper housing 205 includes grip cap 228. In the relaxed position, upper housing 205 partially overlies the proximal, portion of middle housing 201. The distal-most portion of middle housing 201 is fixedly seated in lower housing 202. Also shown in FIG. 10A are upper housing bottom edge 211, travel ridge 216, and window 204. Window 204 preferably is seated within the distal portion of lower housing 202. A second window, not shown, preferably is present on the device on the side opposite of window 204.

Figure 10A:
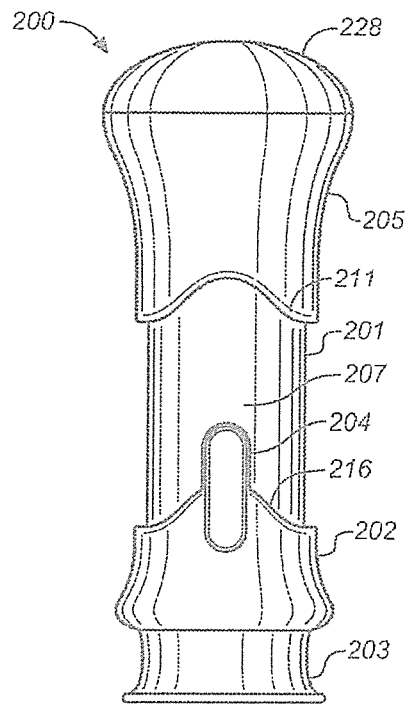
FIG. 10A is a side view of another embodiment of the present invention.
Figure 10B:
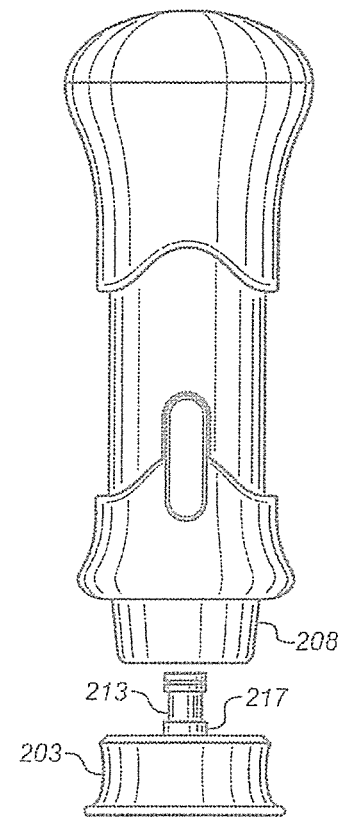
FIG. 10B is a side view of the embodiment of FIG. 10A after cap removal.
Figure 10C:
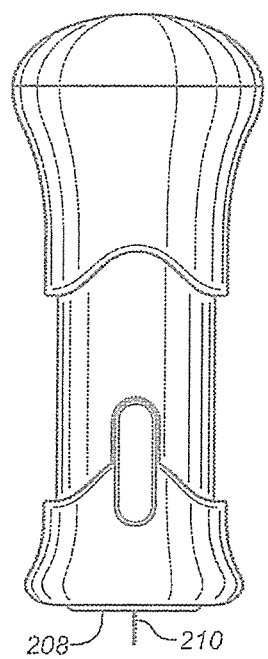
FIG. 10C is a side view of the embodiment of FIG. 10B after the needle guard has been retracted, exposing the needle.

Cap 203 is removably attached to lower housing 202 and, in FIG. 10B, is shown removed from device 200 to expose needle shield 213, needle shield clamp 217 and needle guard 208. During removal of cap 203, needle shield clamp 217 grabs and simultaneously removes needle shield 213 exposing needle guard 208 to the user. When the device user presses the needle guard 208 against the skin, this action causes needle guard 208 to slide upwardly exposing needle 210, as shown in FIG. 10C.

Figure 12:
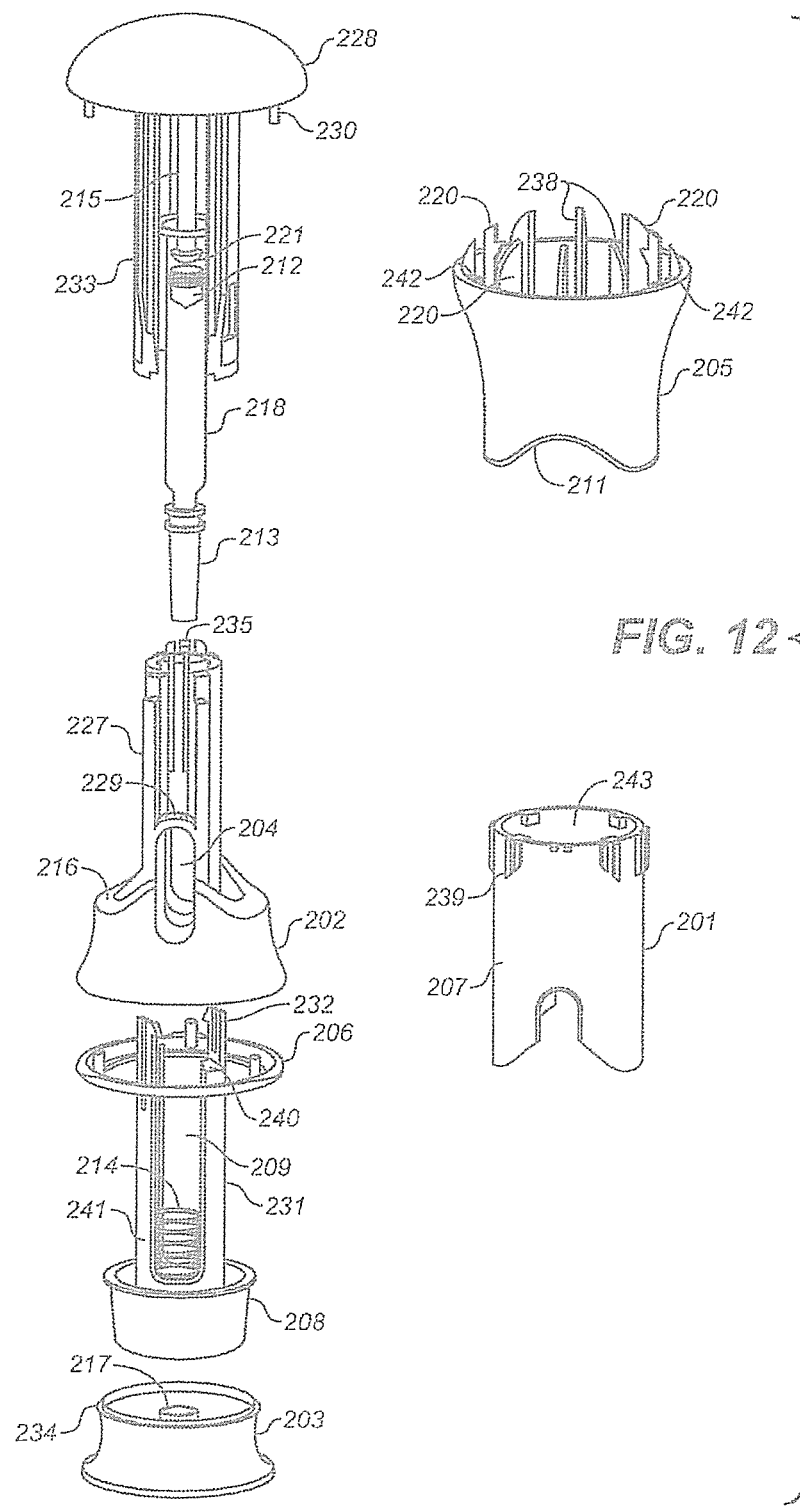
FIG. 12 is a depiction of an exploded view of the embodiment of FIG. 10A.

FIG. 12 is an exploded view of device 200. Grip cap 228 includes grip cap assembly pins 230 that fixedly secure grip cap 228 on upper housing 205. Assembly pins 230 mate with holes 242 in upper housing 205. Preferably, assembly pins 230 are square in cross-section with rounded corners providing an interfering surface between the corners of assembly pins 230 and holes 242. Guides 233 and plunger rod 215, which are integral with and extend downwardly from the inner surface of grip cap 228 as shown. Plunger rod 215 includes a damper 221 at its distal end. Also shown are syringe 218 with plunger 212 and needle shield 213.

In a preferred embodiment, the external surface of grip cap 228 is coated with or formed from, or the entirety of grip cap 228 is formed from, a material capable of providing a soft, non-slip grip for the user. Suitable materials for coating or forming the grip cap include, without limitation, elastomeric materials such as neoprene rubber, urethane, polyurethane, silicone, natural rubber, TPE and the like and combinations thereof.

Upper housing 205 includes click latch 220, handle rib guide 238, and bottom edge 211. For click latch 220, as well as the other latches used in the device, preferably at least two latches are used and the same latches are symmetrically positioned with respect to each other to facilitate smooth movement and operation of the device.

Middle housing 201 is shown in FIG. 12 with body 207 and handle guide slots 239 on the external surface of the proximal portion of body 207. When the device is in use, handle rib guides 238, which are an integral part of upper housing 205, engage with and slide within handle guide slots 239, maintaining smooth and controlled motion of upper housing 205 during drug delivery.

Body 207 may serve as a dose indicator because, as the device is activated, upper housing 205 descends over body 207. When the complete medication dose has been delivered, body 207 is fully obscured by upper housing 205 as shown in FIG. 11C. Preferably body 207 is colored, more preferably with a bright color, or is patterned to provide easily viewed visual feedback to the user that the dosing is progressing or has been completed. Optionally, a scale may be included on body 207 to visually quantify the amount of drug that has been delivered or remains to be delivered.

Figure 13A:
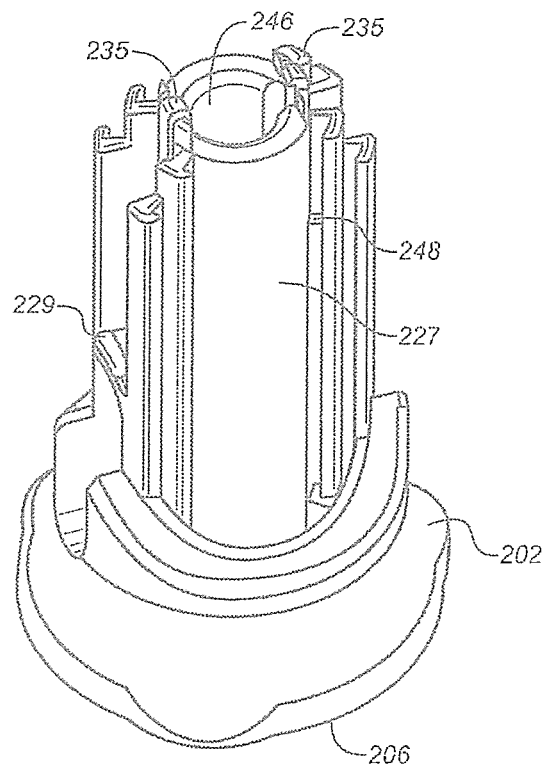
FIG. 13A is a perspective view of the lower housing of the embodiment of FIG. 10A.
Figure 13B:
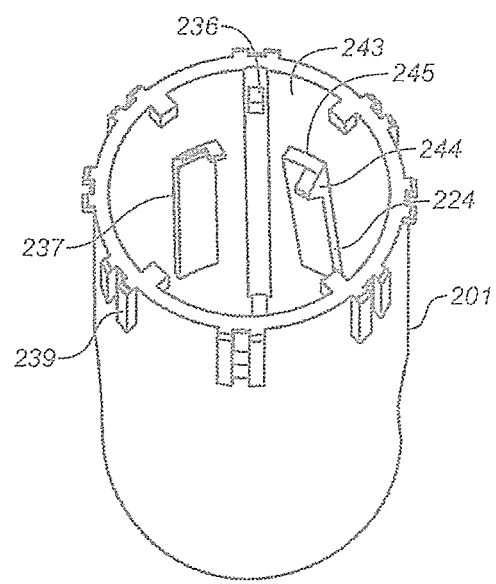
FIG. 13B is a perspective view of the middle housing of the embodiment of FIG. 10A.

With reference to FIG. 13, middle housing 201 also includes grip latches 224, click latch capture slots 236, and needle guard latch 237. Grip latch 224 is a generally rectangular element movably attached at its distal-most portion to the inner surface 243 of middle housing 201 so that it is capable of movement outwardly toward inner surface 243 upon application of force. Grip latch 224 also includes a stop surface 245 and a triangular shaped stop 244 extending inwardly toward the device's center from one corner of its topmost portion. In the device's resting, pre-use position grip latch 224 prevents upper housing 205 from moving with respect to middle housing 201 due to stop 245 interfering with the downward travel of guides 233 of grip cap 228.

With reference to FIGS. 12 and 13, lower housing 202 is shown with lower housing base 206, end of travel ridge 216, window 204, housing latch 229, guide slots 227 and syringe retainer clip 235. Cap 203 removably attaches to lower housing base 206 via cap retainer ring 234. In use, lower housing base 206 contacts the user's skin and, thus, preferably is made of any of the soft flexible materials suitable for use for grip cap 228.

Window 204 provides an opening in lower housing 202 for viewing of the contents of syringe 218. Window 204 is positioned such that the bottom of syringe 218 is visible to the user allowing the user to verify that plunger 212 has reached the end of its travel to the bottom of the syringe. Window 204 may be any convenient size and shape and preferably is oblong in shape with its long axis aligned with the long axis of the device and syringe so that the desired length of the syringe is exposed to view.

Guide slots 227 maintain the alignment of three different components: guides 233 of grip cap 228; grip latch release 231; and needle guard extensions 241. Guide slots 227 ensure smooth activation of the device by maintaining alignment and vertical travel of upper housing 202 and needle guard 208 and reliable latching and unlatching of grip latch 231. Housing latch 229 extending outwardly secures middle housing 201 to lower housing 202 by engaging a recess, that is not shown, in inner surface 243 of middle housing 201. In non-reusable embodiments of the device, the shape of latch 229 and the recess are such that the middle and lower housing cannot be separated. For reusable embodiments, the recess and latch are configured to enable the middle and lower housing to be pulled apart.

Figure 14:
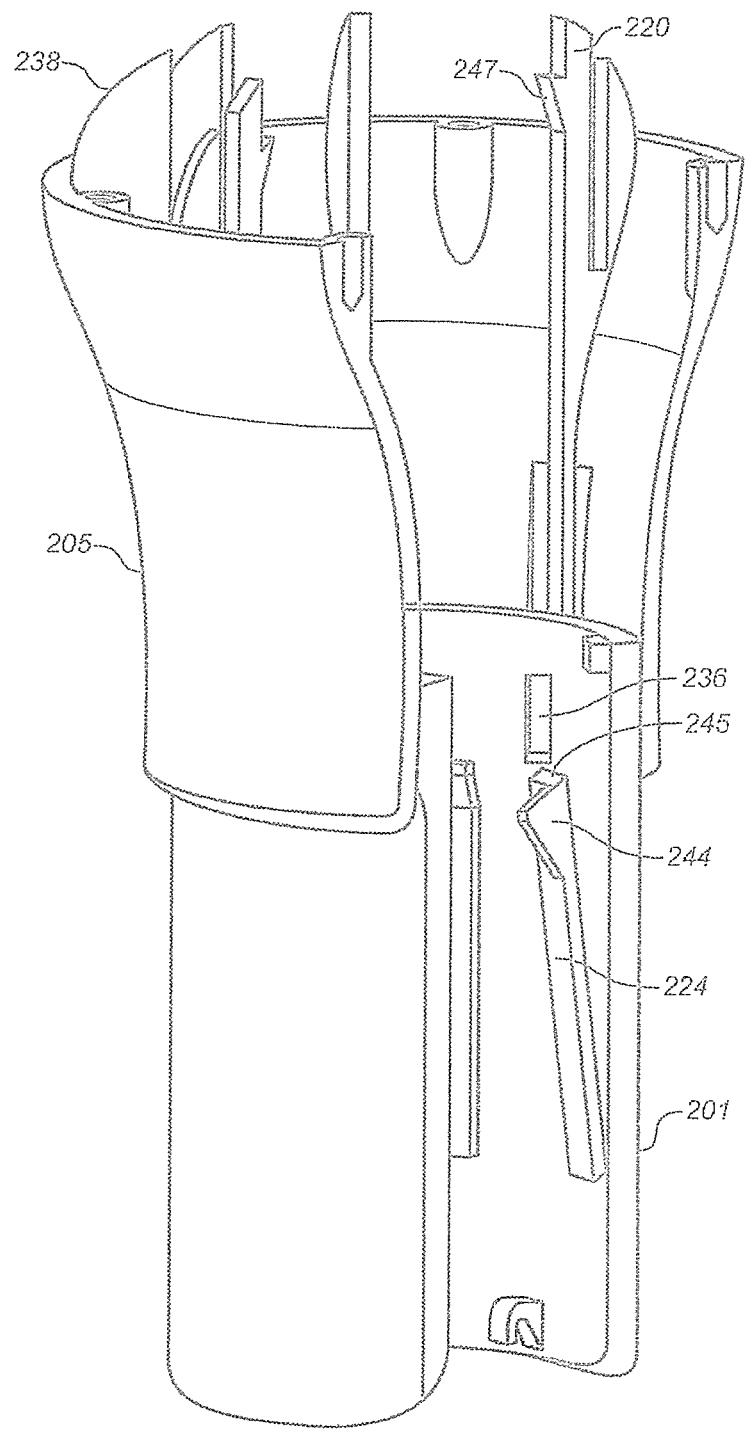
FIG. 14 is a depiction of a partial cross-sectional view of a portion of the upper and middle housings of the embodiment of FIG. 10A.
Figure 15:
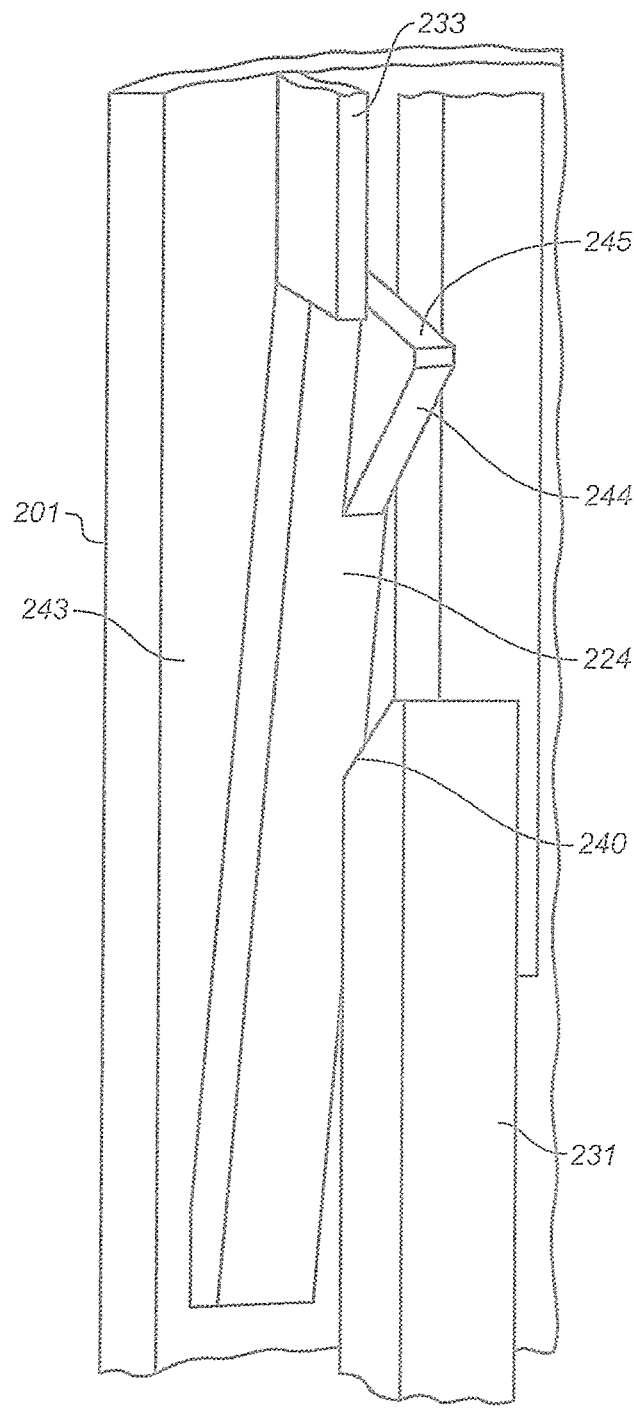
FIG. 15 is a depiction of a latching mechanism of the embodiment of FIG. 10A

Referring to FIG. 12, needle guard 208 includes needle guard slot 209 formed on one side by grip latch release 231 and the other side by needle guard extension 241. Grip latch release 231 includes ramped surface 240. Referring to FIGS. 14 and 15, ramped surface 240 of grip latch release 231 faces outwardly and, as grip latch 231 travels upwardly, engages ramped surface 244 of grip latch 224, which faces inwardly, causing grip latch 224 to deflect outwardly, removing the obstruction to the downward movement of guide 233 and 205.

Needle guard slot 209 permits window 204 to be used to view the syringe and plunger as the plunger acts on the syringe at the end of the plunger's downward stroke. Additionally, needle guard return 214 lies within and at the bottom of a space formed by grip latch release 231 and needle guard extension 241.

Figures 17A, 17B:
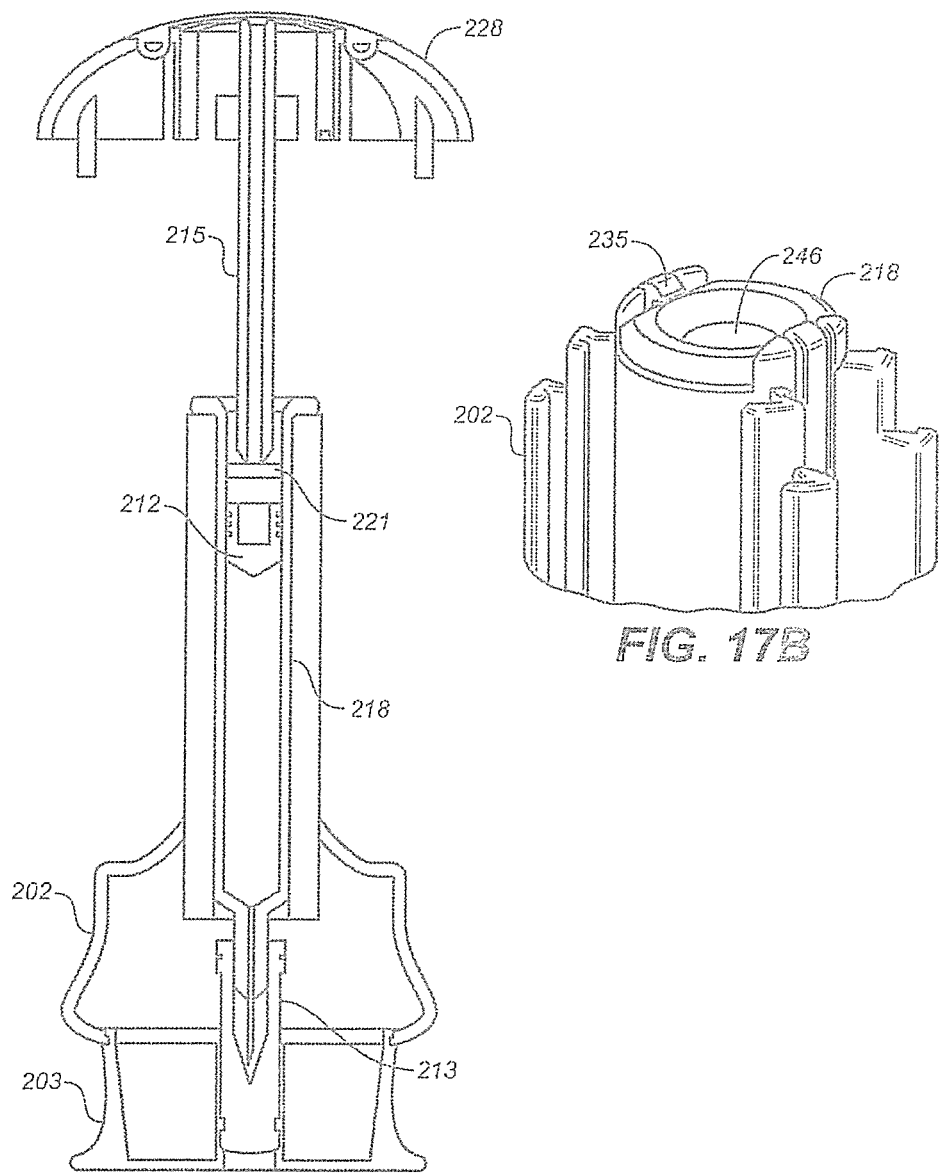
FIG. 17A is a depiction of a cross-sectional view of a portion of the embodiment of FIG. 10A.
FIG. 17B is a depiction of a perspective view of a portion of the lower housing of the embodiment of FIG. 10A.
Figure 18:
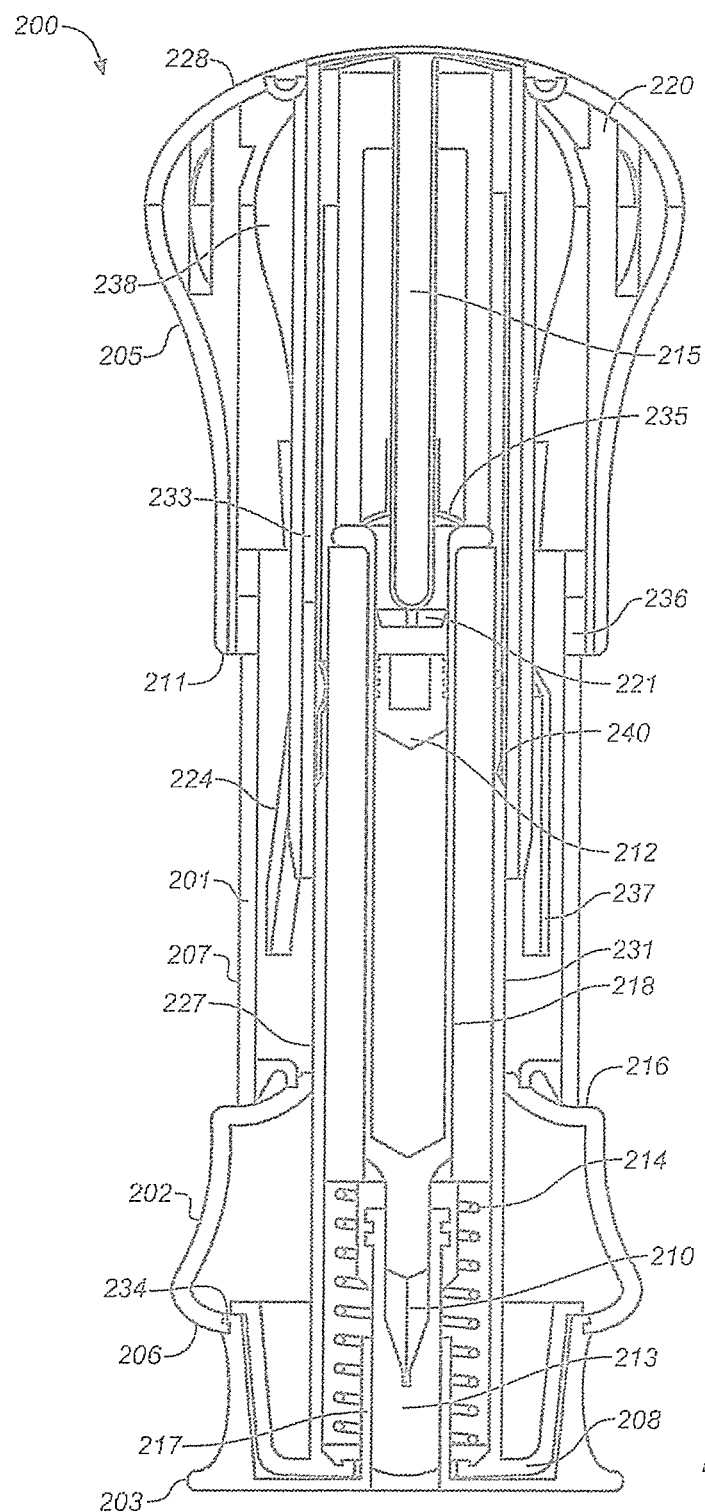
FIG. 18 is a cross-sectional view of the device of FIG. 10A.

An inventive aspect of the device 200 is the way in which syringe 218 is suspended inside the device. With reference to FIGS. 12, 13, and 17, syringe 218 is held between needle shield 213 and damper 221, each of which are flexible components, to protect syringe 218 in the event device 200 is dropped or otherwise mishandled. When the device is assembled, syringe 218 is loosely held within cavity 246 of lower housing 202 by retainer clips 235. Depending on the volume of medication within syringe 218, when the device is in used, there may be some travel of upper housing 205 before damper 221 contacts plunger 212 and, during this initial downward travel, damper 221 acts as an air piston to compress the air in the gap formed between the end of plunger rod 215 and plunger 212, which provides a rate-dependent resistance to motion to the initial downward motion of grip. When damper 221 moves fast, air cannot escape quickly enough to reduce the build-up of air pressure. Damper 221 may optionally include through-holes, that are not shown, therein to allow air to leak past damper 221. Alternatively, a friction-based resistance from the damper without pressure build-up, use a damper in which there is no leak and no rate dependence, or combinations thereof may be used. Upon contact of damper 221 with plunger 212, damper 221 collapses inwardly towards plunger rod 215 reducing the friction between damper 221 and the inside surface of cavity 246.

With reference to FIGS. 10 and 11, when the user desires to use device 200, the user removes cap 203 from lower housing 202, which action simultaneously removes needle shield 213 and exposes needle guard 208. The user grasps device 200 by upper housing 205, places the palm of the hand over grip cap 228 and presses downwardly on grip cap 228 while holding the device 200 against the desired injection site on the body, which pressing action causes needle guard 208 to slide upwardly exposing needle 210. Continuing application of pressure to grip cap 228 results in needle 210 penetrating the user's skin and sub-dermal tissue, stopping when lower housing base 206 contacts the skin surface or when the rim 245 reaches of needle guard 208 reaches the end of its travel within lower housing 202.

With reference to FIG. 15, when needle guard 208 reaches the end of its upward travel within lower housing 202, ramped surface 240 of grip latch release 231 contacts the oppositely facing and complementarily ramped surface 244 of grip latch 224 of middle housing 201 causing grip latch 224 to deflect towards the inner wall 243 of middle housing 201. This action removes stop surface 245 of grip latch 224 from interfering with the downward travel of guide 233 of grip cap 228 freeing guide 233 and allowing upper housing 205 to move downwardly and over middle housing 201.

When upper housing 205 moves downwardly, the medication inside of syringe 218 is delivered through needle 210 as plunger rod 215 and damper 221 of grip cap 228 push downwardly on syringe plunger 212. At the end of the medication delivery, body 207 is substantially completely covered by upper housing 205 and bottom edge 211 of upper housing 205 has mated with the complementarily shaped travel ridge 216 of lower housing 202. Also, plunger rod 215, damper 221, and plunger 212 are clearly visible within window 204. All of these features provide the user with visual confirmation that the drug has been delivered and the hard stop of bottom edge 211 against travel ridge 216 provides a tactile confirmation to the user.

Additionally, a click mechanism is activated at the end of drug delivery to provide audible feedback. With reference to FIG. 14, click latch 220 is deflected outwardly when ramp 247 thereof contacts and slides past the top of middle housing 201. When the ramp 247 moves sufficiently far downwardly, ramp 247 aligns with click latch capture slot 236 and the ramp 247 slips into capture slot 236, which slot extends through the wall at the proximal portion of middle housing 201, and snaps against the outer surface of body 207 of middle housing 201 creating a clicking sound. In non-reusable versions of the device, click latch 220 is permanently captured by capture slot 236 and cannot be reset. In a preferred embodiment, two click latches 220 are positioned at positions 180 degrees opposite of each other in order to provide smooth activation of the device and to enhance the clicking and latching functions.

Figure 16:
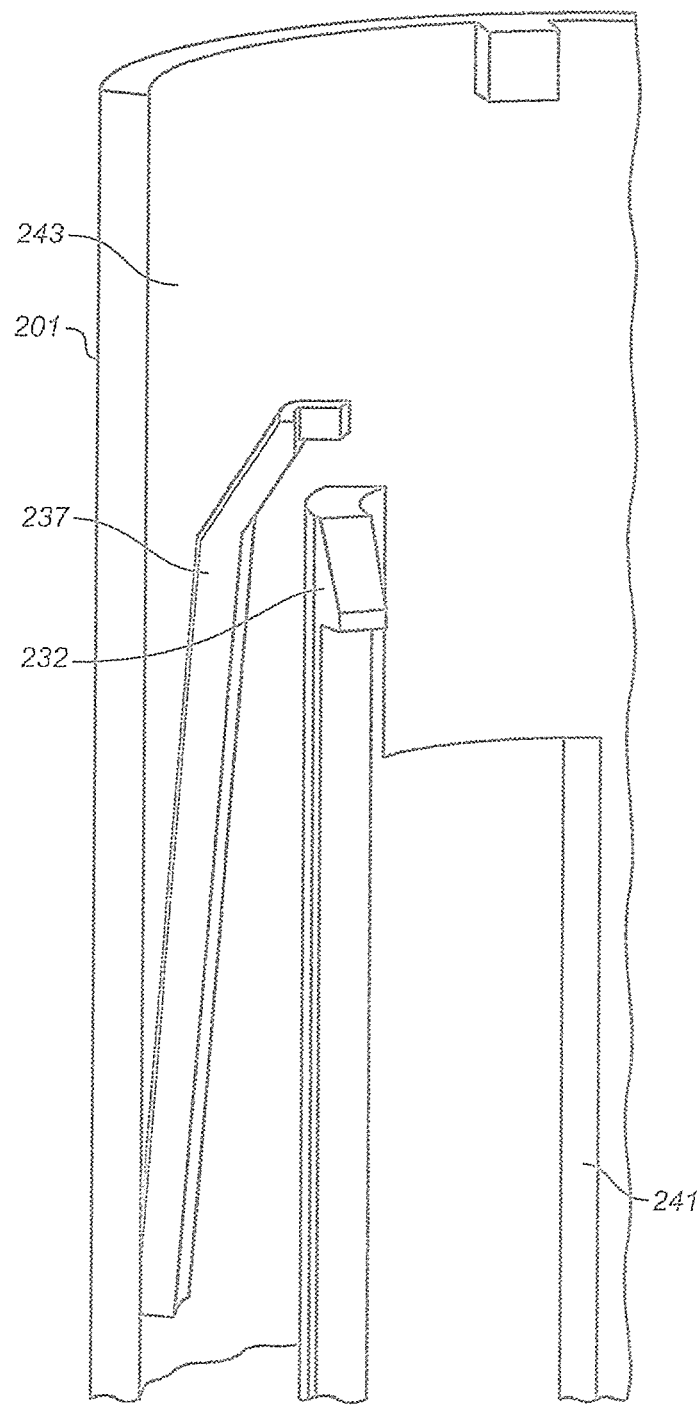
FIG. 16 is a depiction of another latching mechanism of the embodiment of FIG. 10A.

As the user removes device 200 from the skin, needle guard return 214, shown in FIG. 12 as a spring, that was compressed by pressing of device 200 against the user's skin, expands causing needle guard 208 to extend downwardly over needle 210 protecting the user from accidental punctures. In addition to a spring, the needle guard return may be a compressed gas actuator, a hydraulic drive, a wax actuator, an electrochemical actuator, a shape memory alloy, and the like and the combinations thereof. When needle guard 208 is fully extended, needle guard retainer 232 engages stop 248, shown in FIG. 13, on lower housing 202 preventing needle guard 208 from separating from lower housing 202. In FIG. 16 is shown needle guard latch 237 moveably attached at its distal end to the inner surface 243 of middle housing 201. When needle guard 208 is upwardly traveling, needle guard latch 237 is deflected outwardly on contact with the outer surface of guide 233 or of needle guard extension 241. When needle guard 208 travels downwardly and extends to cover needle 210, needle guard latch 237 slips over the top of needle guard extension 241 preventing needle guard 208 from again retracting.

Prior to use, extension guides 233 of grip cap 228 retain needle guard latch 237 in an outwardly deflected position allowing needle guard 208 to retract for insertion of needle 210. Two needle guard retainers 232 and needle guard latches 237 preferably are used and are located 180 degrees apart around the central axis of the device 200. If the device 200 is removed from the skin before delivery of medication is completed, needle guard 208 will extend to cover needle 210 and locks to prevent reuse of the device. In an alternative, reusable embodiment, needle guard 208 extends, but does not lock in place in the event device 200 is removed from the skin before delivery of medication is completed.

Figure 19:
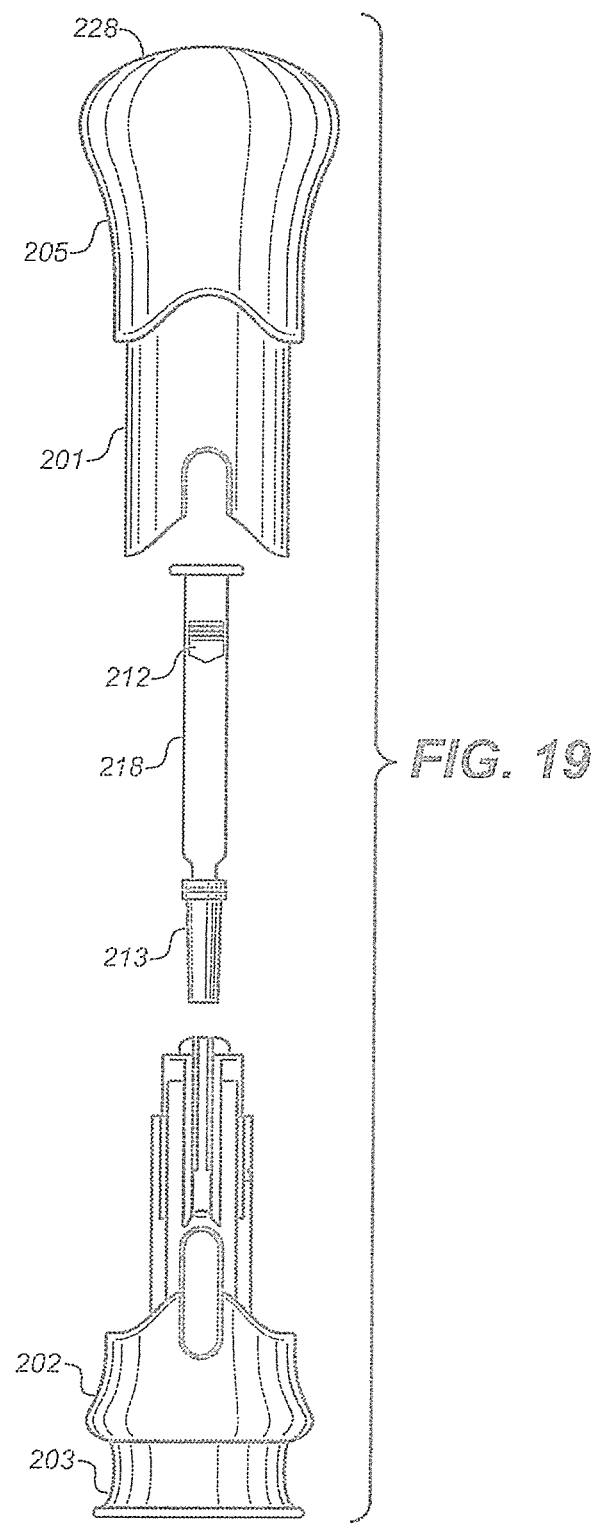
FIG. 19 is an exploded, side view of still another embodiment of the present invention.

FIG. 19 is a depiction of an alternative, reusable embodiment of device 200 in which upper housing 205 and middle housing 201 are separable from lower housing 202. In this embodiment, the user separates the middle and lower housings, inserts syringe 218 into the lower housing and then reattaches the middle and upper housings.

Figure 20:
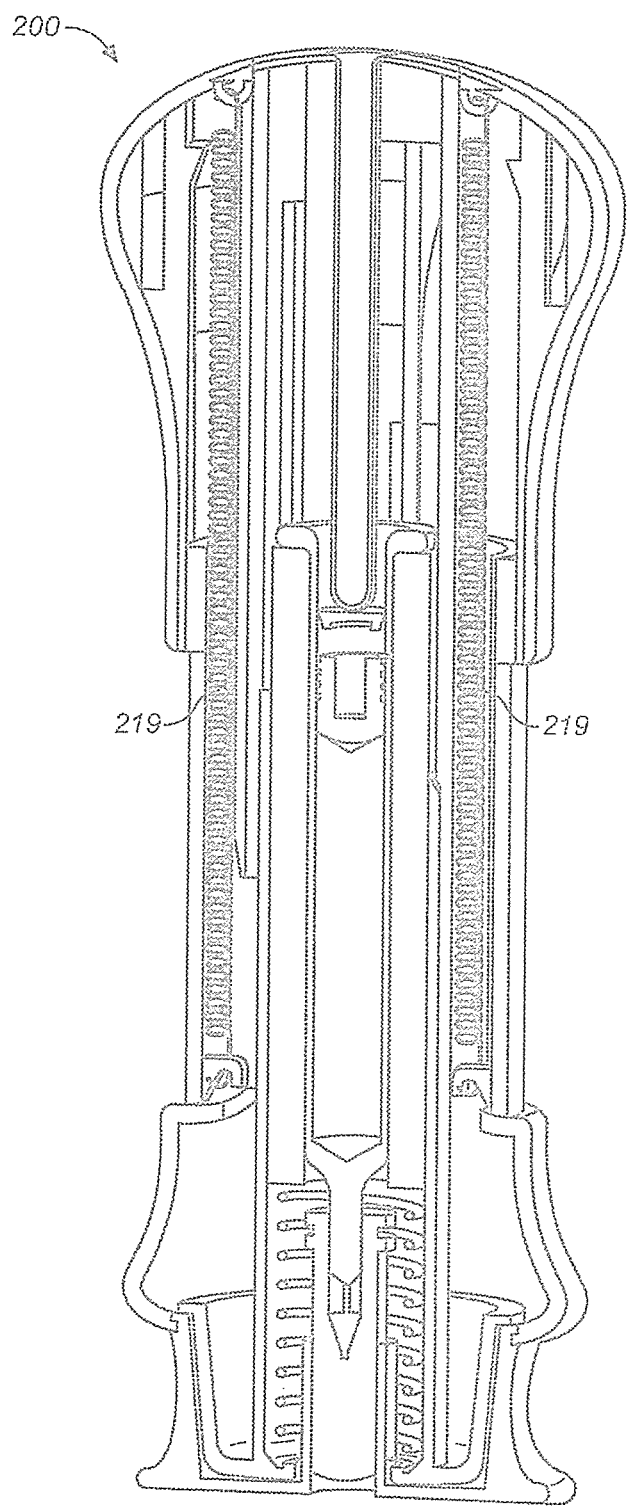
FIG. 20 is a depiction of a cross-sectional, side view of yet another embodiment of the present invention prior to use.

In FIG. 20 is depicted yet another alternative embodiment of device 200 in which an assist drive 219 is included. Assist drive 219 may find its greatest utility in delivering viscous drugs. The assist drive 219 applies a force between upper housing 205 and middle housing 201 exerting a downward force on upper housing sleeve 120. This reduces the amount of downward force the user must apply to grip cap 228 in order to inject the drug. Assist drive 219 may be a spring, a compressed actuator, a hydraulic drive, a wax actuator, an electrochemical actuator, a shape memory alloy or the like or combinations thereof. Alternatively, assist drive may provide sufficient force to inject the drug, without additional force input required by the user, thus providing an injection device in which the needle is manually inserted and the drug is automatically injected in a manner similar to a conventional auto-injector.

In FIG. 21 is depicted an alternative embodiment of lower housing 202 of device 200 in which a resettable clicking mechanism for a reusable device is included. In this embodiment, guide slots 227 engage guide 225 of clicker 222. Clicking device 222 is biased by needle guard return 214. To set clicking device 222, the user presses down on one of clicker guides 225 until clicker latch 226 extends over clicking device 222 holding it down. When grip cap 228 moves downwardly, at the end of travel, guide 233 contacts a ramped surface on clicker latch 226 causing it to deflect inwardly and releasing clicker 222 to travel upwardly under the force of needle guard return 214. A click sound is generated when click surface 223 of clicker 222 contacts lower housing 202 signaling that the drug has been completely delivered. The compressing of needle guard return 214 is increased when needle guard 208 is retracted during injection of the drug, increasing the force applied to the clicking device and the volume of the click sound. Alternatively, the click mechanism can be reset automatically when the user attaches the upper housing to the lower housing upon loading a new syringe into the device.

Figure 22C:
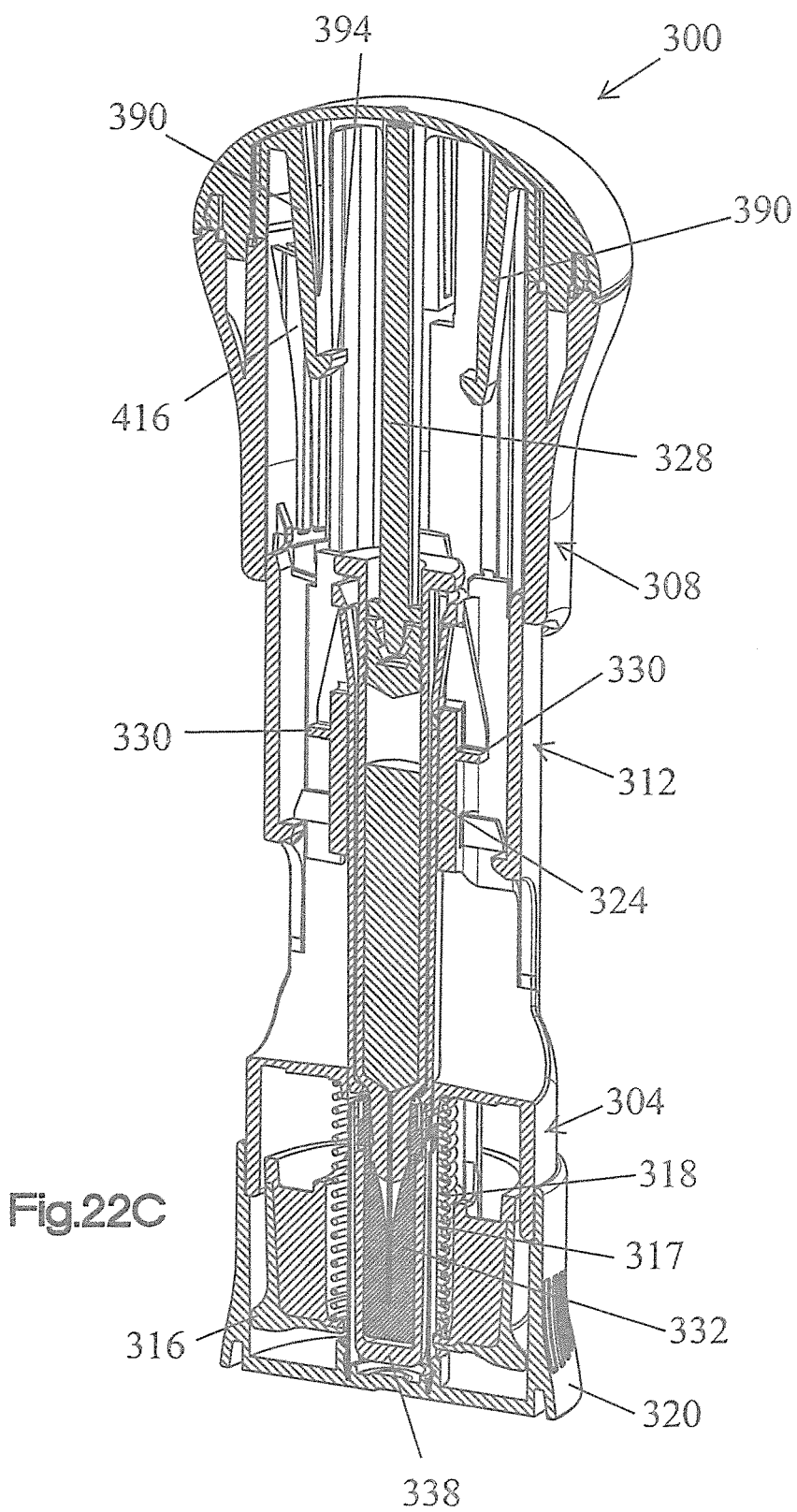
FIG. 22C is a cross-sectional view of the medication delivery device shown in FIG. 22A.

FIGS. 22A-30F depict yet another embodiment of the medication delivery device. As shown in FIGS. 22A-22E, and 23 a delivery device 300 that is configured to deliver a medication defines a central axis A, a proximal end P, and a distal end D that is spaced from the proximal end D along the central axis A. As shown in FIGS. 22A and 22B, the device 300 can include a lower housing 304, an upper housing 308, and a middle housing 312 coupled between the lower housing 304 and the upper housing 308. The device 300 can further include a needle guard 316 that is supported by the lower housing 304 and a cap 320 that is removably coupled to the lower housing 304 such that when the cap 320 is removed, the needle guard 316 is exposed. The needle guard 316 is movable relative to the lower housing 304 along a first direction $X_1$ from a first position whereby a needle 332 of the device 300 is guarded (e.g. as shown in FIG. 22C) to a second position whereby the needle 332 is exposed (e.g. as shown in FIG. 22D). When the device 300 is pressed against the tissue surface, the needle guard 316 is configured to move from the first position to the second position to thereby allow the needle 332 of the device 300 to be inserted into the tissue. As shown in FIGS. 22C-22E and 23, the needle guard 316 includes a needle guard return 317, illustrated as a spring 318 that is configured to cause the needle guard 316 to move from the second position toward a final position along a second direction $X_2$ that is opposite the first direction $X_1$ and over the needle 332 as the needle 332 is removed from the tissue (e.g. as shown in FIG. 22E).

Figure 23:
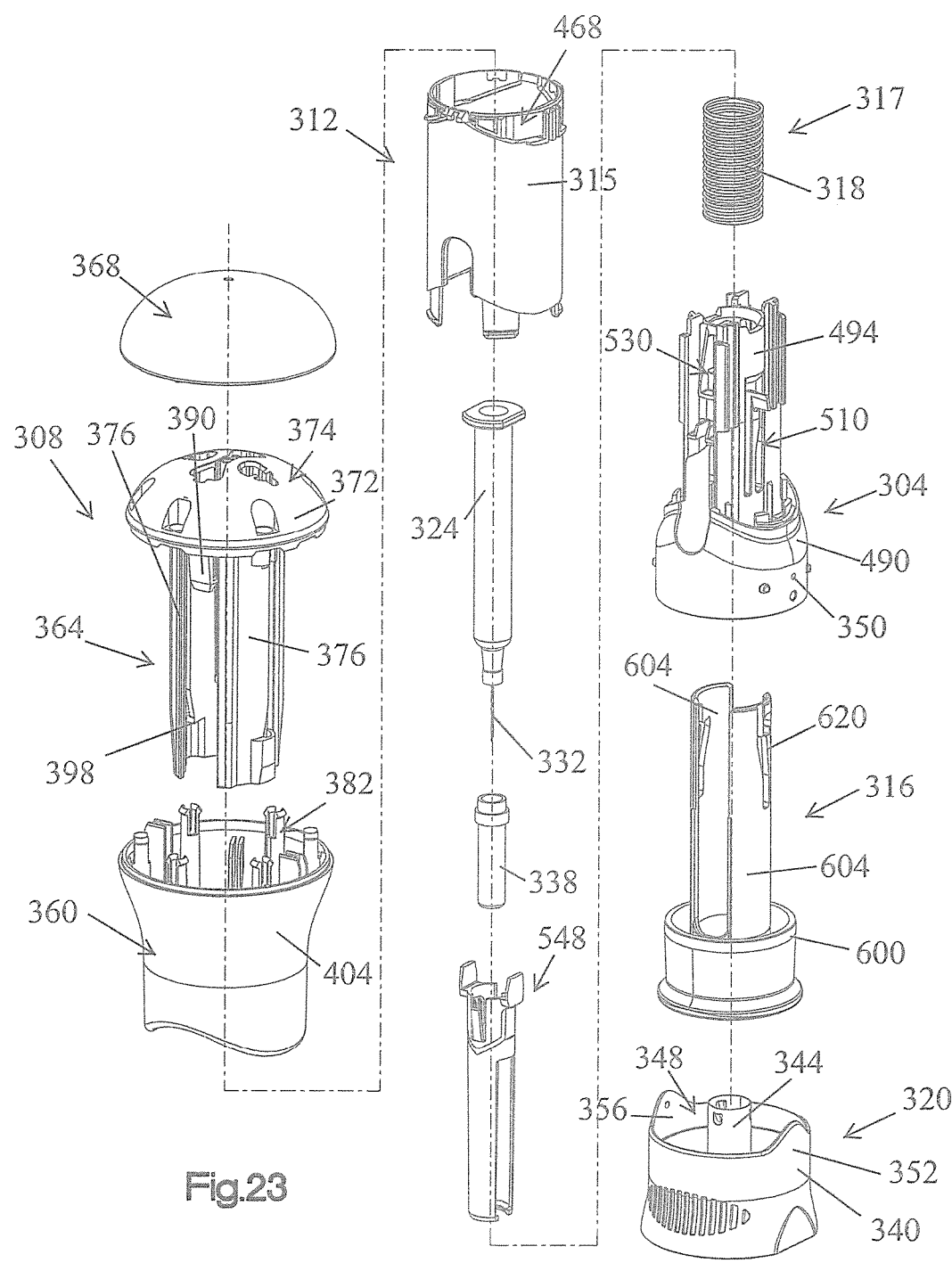
FIG. 23 is an exploded view of the medication delivery device shown in FIG. 22A, including a grip cap, housing body, and skirt of the upper housing, syringe retainer, syringe, and needle shield.

With continued reference to FIGS. 22A, 22B, and 23, the upper housing 308 is supported relative to the lower housing 304 and is configured to receive a manual force and move with respect to the lower housing 304 along the second direction $X_2$ from a pre-use position to a dispensed position in response to the manual force. As shown in FIGS. 22A and 22B the middle housing 312 includes a body 315 that is exposed between the upper housing 308 and the lower housing 304 when the upper housing 308 is in the pre-use position and substantially completely covered by the upper housing 308 when the upper housing 308 is in the dispensed position. Therefore, the upper housing 308 is configured to move along the middle housing body 315 as the upper housing 308 moves toward the dispensed position.

As shown in FIG. 22B, the upper housing 308 can define a first or bottom mating edge or surface 311 and the lower housing 304 can define a second or upper mating edge or surface 313 that mates with the bottom edge 311 of the upper housing 308 when the upper housing is in the dispensed position. The edges 311 and 313 can be sinusoidal as illustrated and can provide visual indication that the upper housing 308 has moved to the dispensed position. It should be appreciated, that the edges 311 and 313 can have any configuration as desired. For example, the edges 311 and 313 can be flat as desired.

With continued reference to FIGS. 22C-22E and 23, the delivery device 300 further includes a syringe 324 that is supported by the lower housing 304 and a plunger rod 328 that is carried by the upper housing 308 and movable with the upper housing 308 so as to advance relative to the syringe 324 when the upper housing 308 is moved along the second direction $X_2$. The syringe 324 is configured to retain a medication and carries the needle 332 that is configured to be inserted into tissue. Advancement of the plunger rod 328 relative to the syringe 324 causes the syringe 324 to deliver the medication out the needle 332 and into the tissue. As shown in FIGS. 22A and 22B, the delivery device 300 further includes at least one window 336, such as a pair of windows 336 that provides an opening into the lower housing 304 for viewing the contents of the syringe 324. As shown in FIGS. 22A, 22B, and 23 the lower housing 304 and the middle housing 312 together define the windows 336 such that the windows 336 are located proximate to a distal end of the device 300. Therefore, the windows 336 are positioned such that the bottom of the syringe 324 is visible to the user thereby allowing the user to verify that the plunger rod 328 has reached the end of its travel to the bottom of the syringe 324. The windows 336 can be oblong along the first direction $X_1$ as illustrated, though it should be appreciated, that the windows 336 can have any size and shape as desired.

As shown in FIG. 23, the cap 320 is removably attached to the lower housing 304 such that removal of the cap 320 exposes the needle guard 316 and removes a needle shield 338 from the syringe 324 to thereby expose the needle 332 within the needle guard 316. As shown in FIG. 23, the cap 320 includes a cap body 340 and a needle shield clamp 344 attached to the cap body 340. The cap body 340 defines a cavity 348 that receives the needle guard 316 when the cap 320 is attached to the lower housing 304 and a cap retainer ring 352 that grips the lower housing 304 to thereby removably couple the cap 320 to the lower housing 304. As shown in FIG. 23, the cap retainer ring 352 defines a pair of detents 356 that are configured to receive a pair of protrusions 350 defined by the lower housing 304 to thereby removably couple the cap 320 to the lower housing 304. To remove the cap 320 the lower housing 304 can define a pair of bumps on either side of the protrusions 350 that allow the cap to be twisted off. For example, the bumps can engage cam surfaces on the cap such that when the cap is twisted the bumps push the cap away from the lower housing 304. It should be appreciated, however, that the cap retainer ring 352 can include any features that removably couple the cap 320 to the lower housing 304 as desired.

With continued reference to FIGS. 22C and 23, the needle shield clamp 344 can be coupled to the cap body 340 within the cavity 348. The needle shield clamp 344 is configured to grip the needle shield 338 when the cap 320 is coupled to the lower housing 304. The needle shield 338 is attached to the syringe 324 such that the needle shield 338 encloses the needle 332. When the cap 320 is removed from the lower housing 304, the needle shield clamp 344 grips the needle shield 338 such that the needle shield 338 is removed from the lower housing 304 along with the cap 320. When the cap 320 is removed, the device 300 can be positioned against a tissue surface and subsequently activated so as to inject the medication into the tissue.

Now referring to FIGS. 23, 24A-24C, the upper housing 308 can include a skirt 360, a housing body 364 mounted to the skirt 360, and a grip cap 368 mounted to the housing body 364. As shown in FIGS. 24A and 24B, the upper housing 308 and in particular the housing body 364 includes a grip cap mounting member 372 and a pair of guides 376 that extend distally from the grip cap mounting member 372 along the second direction $X_2$. As shown in FIG. 23, the grip cap 368 can be coupled to the grip cap mounting member 372 and the guides 376 can extend through the skirt 360 when the housing body 364 is mounted to the skirt 360.

The grip cap mounting member 372 can be dome shaped so as to define a substantially convex proximal surface 374 and a distal surface 375 that is opposite the proximal surface 374. The grip cap 368 can also be domed shape and can be mounted to the grip cap mounting member 372 such that the grip cap 368 overlies the proximal surface 374. As shown in FIG. 24A, the mounting member 372 can include a plurality of fixation members 380 that extend from the distal surface 375. The fixation members 380 can each define an aperture 381 that is configured to receive a respective fixation member such as a locking pin 382 defined by the skirt 360 to thereby couple the housing body 364 to the skirt 360. It should be appreciated, however, that the fixation members 380 and 382 can have any configurations as desired. For example, the fixation members 380 of the mounting member 372 can define locking pins and the fixation members 382 of the skirt 360 can define apertures. It should also be appreciated, that the grip cap 368 and the housing body 364 can be integrally formed as desired and that the grip cap 368 and mounting member 372 can have any shape as desired.

Figure 22D:
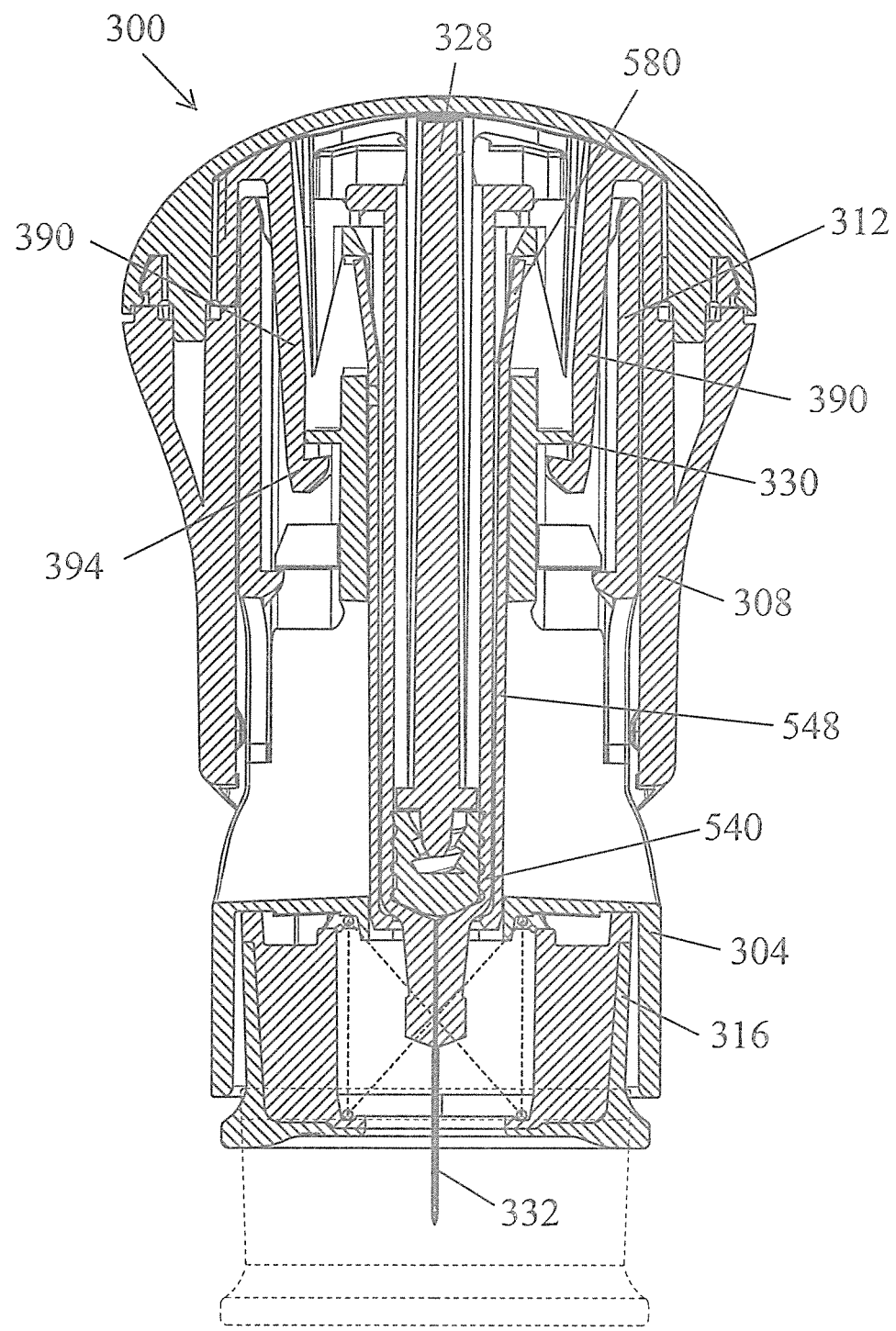
FIG. 22D is a cross-sectional view of the medication delivery device shown in FIG. 22B with the needle guard in the second position whereby the needle is exposed.
Figure 22E:
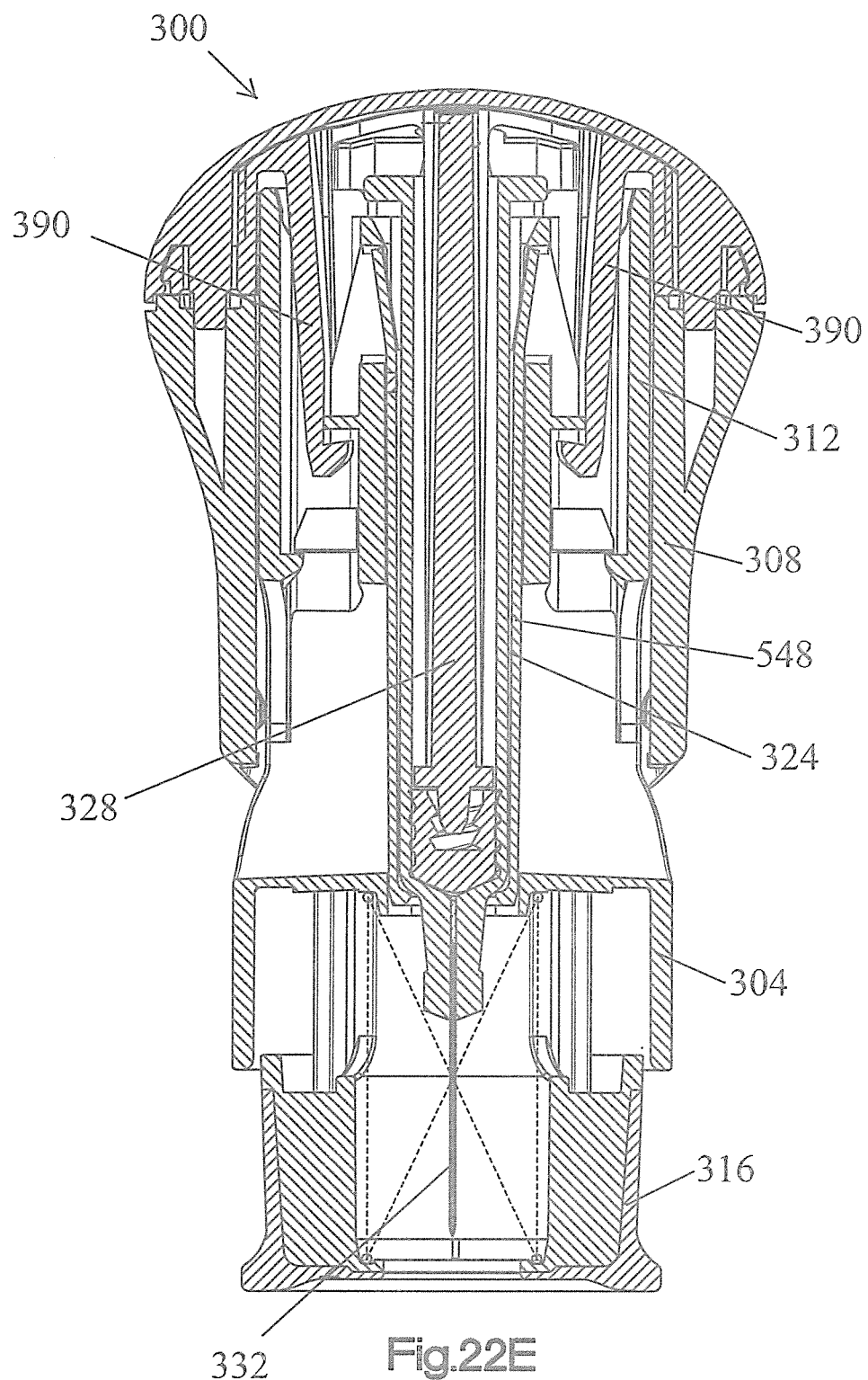
FIG. 22E is a cross-sectional view of the medication delivery device shown in FIG. 22D with the needle guard in the final position whereby the needle is encapsulated.

As shown in FIG. 24A, the upper housing 308 can further include at least one locking latch 390, such as a pair of locking latches 390 that extend from the distal surface 375 of the mounting member 372 and toward the lower housing 304. The locking latches 390 are configured to lock the upper housing 308 in the dispensed position after the upper housing 308 has been moved from the pre-use position to the dispensed position so as to prevent reuse of the device 300. The locking latches 390 can be elastically flexible and can each include a flexing member 392 that extends from the mounting member 372 and a protrusion 394 that extends from a distal end of the flexing member 392 toward the central axis A. As shown in FIGS. 22C-22E the locking latches 390 face each other such that the protrusions 394 extend toward each other along a direction that is transverse to the second direction $X_2$. As shown in FIGS. 22C-22E, as the upper housing 308 is moved along the middle housing 312, the locking latches 390 will engage the lower housing 304 and flex away from each other. When the upper housing 308 reaches the dispensed position the locking latches 390 will move back toward each other such that the protrusions 394 engage a corresponding latch member of the lower housing 304 to thereby lock the upper housing 308 in the dispensed position. When the locking latches 390 engage the corresponding latch members an audible click sound may be produced to thereby signify to the user that the injection is complete. It should be appreciated, however, that the locking latches 390 can have any configuration as desired and that the upper housing 308 can have any number of locking latches as desired. For example, the upper housing 308 can include a single locking latch as desired.

As shown in FIGS. 22C, 23, and 24A-24B each guide 376 of the housing body 364 extends through the skirt 360 and into the middle housing 312. Each guide 376 can include a guide body 377 that is elongate along the second direction $X_2$ and extends from the mounting member 372 such that the guides 376 face each other along a direction that is transverse to the second direction $X_2$. The guides 376 are configured to temporarily interfere with the lower housing 304 so as to maintain the upper housing 308 in the pre-use position until the needle guard 316 has moved to the second position and the needle 332 is inserted into the tissue. In this way, unintentional dispensing of the medication may be avoided.

As shown in FIG. 24B, each guide 376 can define an abutment surface 398 that at least partially faces the lower housing 304 and a channel 400 that extends through the guide body 377 from a distal end of the guide body 377 and toward a proximal end of the guide body 377. The abutment surfaces 398 are configured to engage the lower housing 304 when the upper housing 308 is in the pre-use position to thereby maintain the upper housing 308 in the pre-use position until the needle guard 316 is moved to the second position. The abutment surfaces 398 can be disposed proximate to the distal ends of the guide bodies 377. The abutment surfaces 398 can define a plane that is perpendicular to the first direction and can include an angled portion that defines a ramp that leads into a respective channel 400. The channels 400 extend completely through the guide bodies 377 along a direction that is transverse to the second direction $X_2$ and extend along a substantial portion of the guide bodies 377 along the second direction $X_2$. The channels 400 are configured to act as a relief or a guide for the lower housing 304 when the interference between the upper housing 308 and the lower housing 304 is removed and the upper housing 308 moves toward the dispensed position. That is, the portion of the lower housing 304 that interferes with the upper housing 308 will move within the channels 400 when the interference is removed and the upper housing 308 moves toward the dispensed position. It should be appreciated, however, that the abutment surfaces 398 and channels 400 can have any configurations as desired. For example, the abutment surfaces 398 can be angled and the channels 400 can extend into but not completely through the guide bodies 377 as desired.

As shown in FIG. 24C, the skirt 360 includes a skirt body 404 that has an inner surface 408 that defines a channel 412 that extends completely through the skirt body 404 along the second direction $X_2$. The upper housing 308 is coupled to the middle housing 312 such that the middle housing 312 is received within the channel 412 and the middle housing 312 is configured to move through the channel 412 as the upper housing 308 is moved toward the dispensed position. As shown in FIG. 24C, the skirt 360 includes at least one friction member 416, such as four friction members 416 that extend from the inner surface 408 and toward the central axis A. The friction members 416 are configured to interfere with respective friction members defined by the middle housing 312 to thereby create a friction force as the upper housing 308 moves from the pre-use position toward the dispensed position. The friction force adds resistance when the manual force is applied to the upper housing 308 to thereby prevent the upper housing 308 from moving suddenly along the second direction $X_2$. For example, the friction force may prevent the upper housing 308 from moving suddenly in situations where the syringe 324 is only partially filled with medication and the plunger rod 328 is not in contact with the plunger that is within the syringe 324. The friction force created by the friction members should be greater than or equal to the force of the compressed needle guard spring 318 when the needle guard 316 is in the second position to thereby prevent the needle guard spring 318 from lifting the lower housing 304 and pulling the needle 332 out of the tissue prior to the plunger rod 328 contacting the plunger. It should be appreciated, however, that the friction force can be any desired force. For example, the skirt 360 and middle housing 312 can be void of friction members such that the friction force is substantially zero. It should be further appreciated, that the skirt 360 can define any number of friction members 416 as desired.

With continued reference to FIG. 24C, each friction member 416 can define a rail 420 that protrudes from the inner surface 408. As shown in FIG. 24C, each rail 420 can taper as the rail 420 extends from a distal end of the skirt 360 toward a proximal end of the skirt 360. Therefore, the frictional force can be greater when the upper housing 308 begins moving from the pre-use position than the frictional force when the upper housing 308 is near the dispensed position. It should be appreciated, however, that the rails 420 can have any configuration as desired. For example, the rails 420 can be void of a taper such that the friction force between the upper housing 308 and middle housing 312 is constant along the entire movement of the upper housing 308.

Now in reference to FIGS. 25A and 25B, the middle housing body 315 includes a sidewall 464 and at least one friction member 468, such as four friction members 468 that are carried by the sidewall 464. Each friction member 468 is configured to interfere with a respective one of the friction members 416 of the upper housing 308. As shown in FIG. 25A each friction member 468 can be configured as a cantilevered portion 472 that is coupled to the sidewall 464 at a hinge 474 such that each cantilevered portion 472 is configured to flex relative to a central axis of the middle housing 312 (e.g. the central axis A) as the upper housing 308 moves toward the dispensed position. As shown in FIG. 25A, the sidewall 464 is substantially cylindrical and includes four slots 478 that each defines a respective cantilevered portion 472. Each slot 478 extends from a proximal end of the middle housing body 315 and terminates at a respective hinge 474. In the illustrated embodiment, the hinges 474 are oriented such that the cantilevered portions 472 flex about respective axes that are parallel to the central axis A. As shown in FIG. 25A, the cantilevered portions 472 define first and second pairs of cantilevered portions each having a first cantilevered portion 472a and a second cantilevered portion 472b. The first and second cantilevered portions 472a and 472b of each pair extend away from each other. That is the first cantilevered portions 472a of the first and second pairs extend clockwise about the sidewall 464 and the second cantilevered portion 472b of the first and second pairs extend counterclockwise about the sidewall 464. Therefore, each cantilevered portion 472 can be curved so as to define a radius with respect to the central axis A. It should be appreciated, however, that the cantilevered portions 472 can have any configuration as desired and the hinges 474 can have any configuration as desired. It should be further appreciated, that the friction members 468 are not limited to cantilevered portions 472 and can include any configurations as desired. For example, the friction members 468 can be elastomeric pads on an external surface of the sidewall 464.

With continued reference to FIGS. 25A-25B, each cantilevered portion 472 can be located proximate to the proximal end of the middle housing 312. Each cantilevered portion 472 can include an outer elastomeric portion 480 that is configured to be in contact with a respective rail 420.

The elastomeric portions 480 can be used to increase the friction coefficient of the surfaces of the cantilevered portions 472 that are in contact with the rails 420 to thereby modify the resistance. As shown in FIG. 25C, initially, when the upper housing 308 begins to move from the pre-use position the thicker portion of the rails 420 are in contact with the elastomeric portions 480 such that the cantilevered portions 472 flex inward toward the central axis A and apply a biasing force against the rails 420. The interference between the rails 420 and the cantilevered portions 472 creates a friction force that resists the movement of the upper housing 308 toward the dispensed position. As the upper housing 308 moves further toward the dispensed position, the rails 420 taper such that the biasing force against the rails 420 decreases and the resistance to the downward movement of the upper housing 308 is lessened.

Now in reference to FIGS. 26A and 26B, the lower housing 304 includes a base 490 and a lower housing body 494 that extends from the base 490 along the first direction $X_1$. The base 490 includes a skin facing surface 498 that is configured to face an individual's skin when the needle 332 is inserted into the tissue. The base 490 further defines a cavity 502 that extends into the skin facing surface 498 and is configured to receive the needle guard 316 when the needle guard 316 is moved to the second position. The lower housing body 494 defines a pair of first channels 506a that extend along the lower housing body 494 along the first direction $X_1$ and a pair of second channels 506b that extend along the lower housing body 494 along the first direction $X_1$ adjacent the first channels 506a. Each channel 506a is sized to receive a respective guide 376 of the upper housing 308 such that the guides 376 advance within the first channels 506a along the second direction $X_2$ as the upper housing 308 is moved toward the dispensed position. The second channels 506b are configured to receive portions of the needle guard 316 such that the portions of the needle guard 316 are disposed between the lower housing body 494 and the guides 376 and movable within the channels 506b along the first and second directions $X_1$ and $X_2$.

As shown in FIGS. 26A and 26B, the lower housing 304 further includes at least one housing latch 510, such as a pair of housing latches 510 that releasably interfere with the upper housing 308 when the upper housing 308 is in the pre-use position so as to prevent the upper housing 308 from moving toward the dispensed position. As shown in FIG. 26B, each housing latch 510 includes a leg 512 that extends upward from a respective portion of the lower housing body 494 and a protrusion 514 that extends from a proximal end of the leg 512 away from the central axis A and into the channels 400 defined by the guides 376.

The housing latches 510 are elastically flexible such that the housing latches 510 are configured to flex or otherwise move out of interference with the upper housing 308 as the upper housing 308 moves from the pre-use position and toward the dispensed position. In particular, the protrusions 514 engage the abutment surfaces 398 of the guides 376 to thereby prevent the upper housing 308 from moving toward the dispensed position. When needle guard 316 has moved to the second position and the housing latches 510 are free to flex, movement of the upper housing 308 toward the dispensed position causes the protrusions to move into and along the channels 400 of the guides 376 and thus out of interference with the upper housing 308. It should be appreciated, that the housing latches 510 can have any configuration as desired and can extend from any portion of the lower housing body 494. For example, each leg 512 can extend downward from a respective portion of the lower housing body 494.

With continued reference to FIGS. 26A and 26B, the lower housing 304 further includes at least one latch member 530, such as a pair of latch members 530 that are configured to mate with the locking latches 390 of the upper housing 308 when the upper housing 308 is in the dispensed position. As shown in FIG. 26A, each latch member 530 can define a ramp 532 that extends from the lower housing body 494 and a shelf 534 at a distal end of the ramp 532. The shelf 534 defines a surface that faces the distal end of the device. As the upper housing 308 is moved toward the dispensed position, the protrusions 394 of the locking latches 390 will ride along the ramps 532 and flex away from each other. When the upper housing 308 reaches the dispensed position, the locking latches 390 will snap over the latch members 530 and return substantially to their original positions such that the protrusions 394 engage the shelves 534 to thereby lock the upper housing 308 in the dispensed position. In particular, the protrusions 394 abut the surfaces of the shelves 534 so as to prevent the upper housing 308 from moving back toward the pre-use position. It should be appreciated, however, that the latch members 530 can have any configuration as desired. For example, the latch members 530 can be slots defined in the lower housing body 494 that receive the protrusions 394.

The contact between the protrusions 394 of the locking latches 390 and the ramps 532 can create a friction force that adds to the resistance to the downward manual force that is applied to the upper housing 308 to move the upper housing 308 to the dispensed position. In this way the locking latches 390 and latch members 530 can also be considered friction members. That is, the rails 420 and the cantilevered portions 472 can be considered primary friction members and the locking latches 390 and latch members 530 can be considered secondary friction members.

Figure 27C:
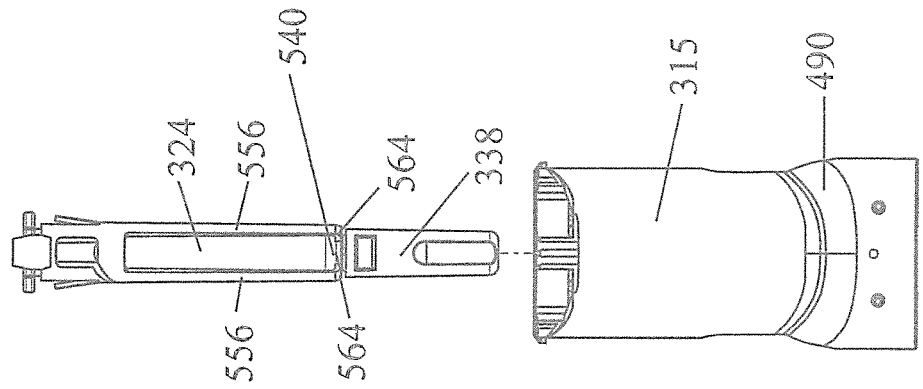
FIG. 27C is a perspective view of the syringe and syringe retainer combination of FIG. 27B being inserted into the lower housing.
Figure 27B:
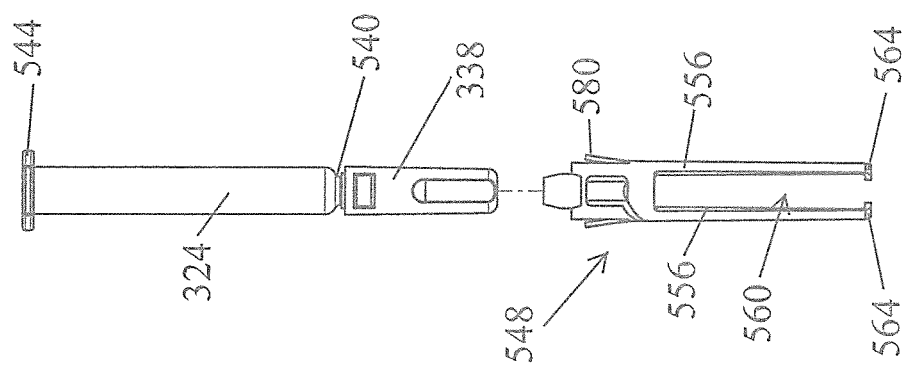
FIG. 27B is a perspective view showing the syringe being inserted into the syringe retainer of FIG. 27A.
Figure 27A:
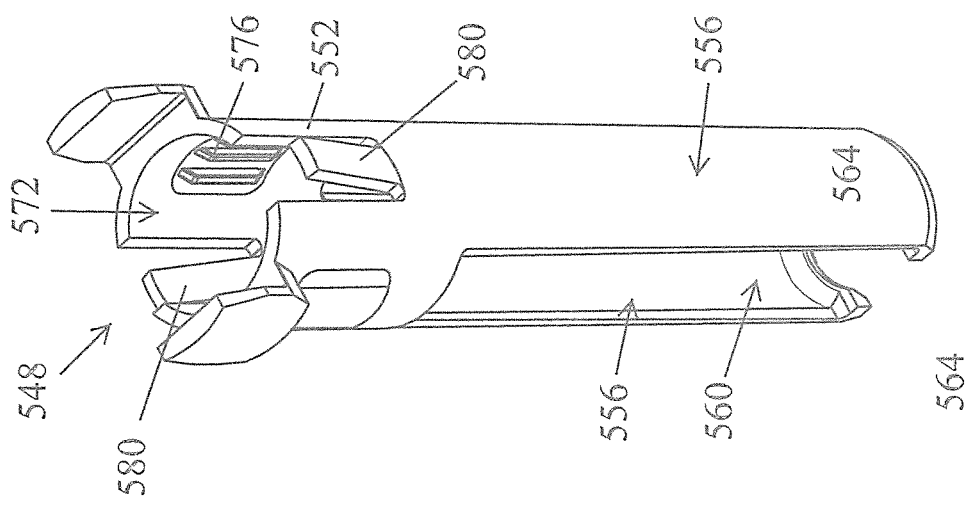
FIG. 27A is a perspective view of the syringe retainer shown in FIG. 23, the syringe retainer being configured to retain the syringe.

Now in reference to FIGS. 23 and 27A-27C, the syringe 324 can include a bottom shoulder 540 that is proximate the needle 332 and an upper rim 544 spaced from the bottom shoulder 540 along the first direction $X_1$. As shown in FIGS. 27A-27C, the device 300 can further include a syringe retainer 548 that is configured to receive the syringe 324 and support the syringe 324 at the bottom shoulder 540. The syringe retainer 548 can include a body 552 and a pair of elastically flexible legs 556 that extend from the body along the second direction $X_2$. The elastically flexible legs 556 are spaced from each other along a direction that is perpendicular to the second direction $X_2$ so as to define a gap 560 between the elastically flexible legs 556. Each elastically flexible leg 556 includes a tab 564 that extends toward the other leg 556 such that when the syringe 324 is moved through the gap 560 along the second direction and toward a seated position, the elastically flexible legs 556 move away from each other, and when the syringe 324 is in the seated position, the elastically flexible legs 556 move back toward each other so that the tabs 564 engage the bottom shoulder 540 of the syringe 324. Once the syringe retainer and retainer combination are inserted into the lower housing 304, the flexible legs 556 are held in place and can no longer flex outward thus supporting the syringe 324. In the illustrated embodiment the tabs 564 are disposed at the distal ends of the legs 556. It should be appreciated, however, that the tabs 564 can be disposed anywhere along the legs 556 as desired.

With continued reference to FIG. 27A, the retainer 548 further includes an aperture 572 that extends through the body 552 and into the gap 560 and at least one grip 576 that is carried by the body 552 within the aperture 572. The at least one grip 576 is configured to abut the syringe 324 so as to prevent the syringe 324 from moving through the gap 560 along the first direction $X_1$ after the syringe 324 is in the seated position. The grips 576 can be elastomeric portions, ribs, or any other structure capable of preventing the syringe 324 from backing out of the gap.

As shown in FIGS. 27A and 22C, the retainer 548 further includes at least one locking tab 580, such as a pair of locking tabs 580, that extend outward from the body 552 away from the central axis A. The locking tabs 580 are configured to abut the lower housing 304 to thereby lock the syringe retainer 548 within the lower housing 304. The locking tabs 580 can be flexible such that as the retainer 548 is seated in the lower housing 304, the locking tabs 580 flex toward the central axis A and subsequently move back to their original position when the retainer 548 is fully seated within the lower housing 304 such that the locking tabs 580 engage respective portions of the lower housing 304 to thereby lock the retainer 548 and syringe 324 within the lower housing 304. It should be appreciated, however, that the retainer 548 can have other configurations as desired. For example, the locking tabs 580 could extend from the legs 556 as desired.

Figure 28:
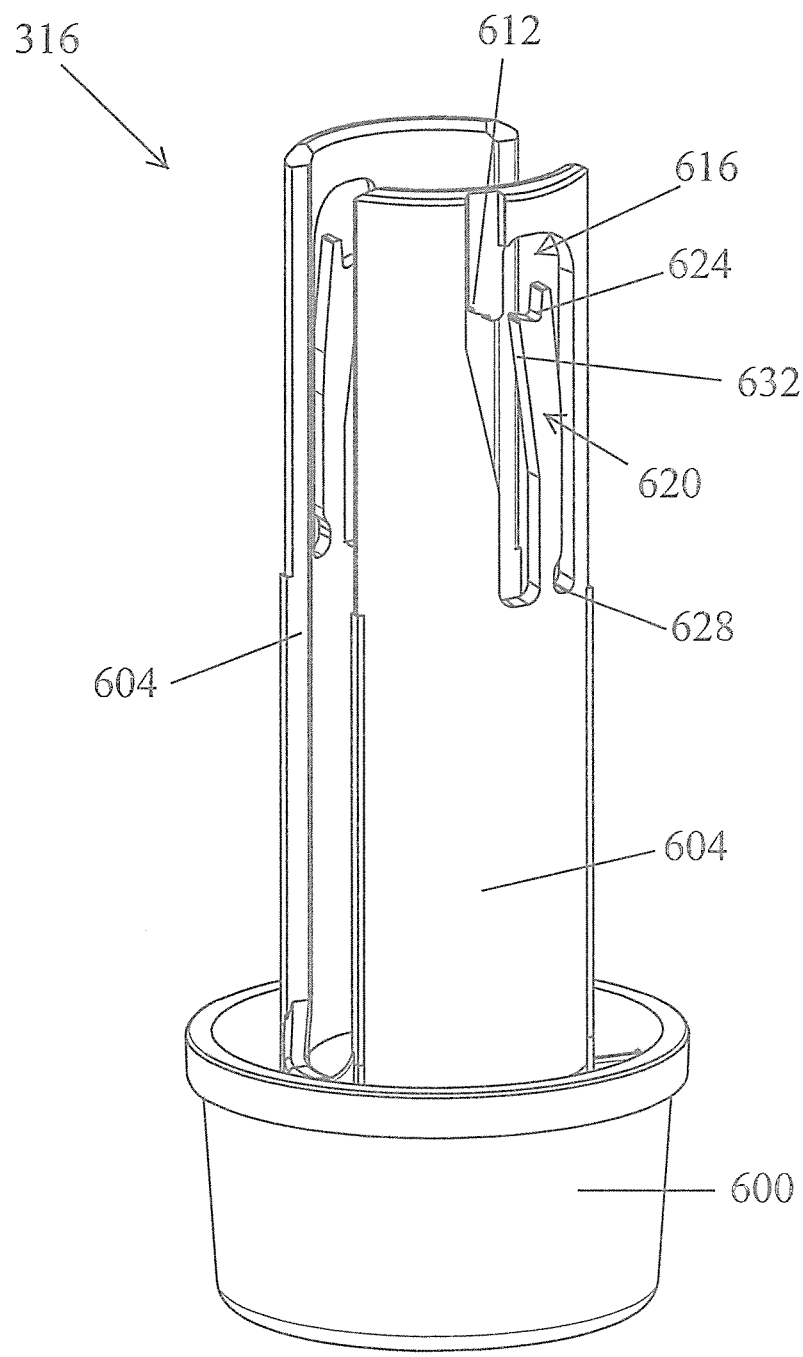
FIG. 28 is a perspective view of the needle guard shown in FIG. 23, the needle guard including a pair of extensions that each includes a stop that maintains a respective housing latch in interference with the guides of the upper housing, and a needle guard latch that is configured to interfere with the housing latch after the needle guard moves from the second position to the final position.

Now in reference to FIGS. 23, 22C-22E, and 28, the needle guard 316 is movable relative to the lower housing 304 along the first direction $X_1$ from the first position to the second position when the needle guard 316 is pressed against a skin surface, and subsequently movable along the second direction $X_2$ from the second position to a final position when the device 300 is removed from the skin surface. As shown in FIG. 28, the needle guard 316 includes a housing 600 and a pair of extensions 604 that extend from the housing 600 along the first direction $X_1$. The housing 600 houses the needle 332 when the needle guard 316 is in the first position and final positions. As the needle guard 316 moves to the second position, the needle 332 protrudes from the housing 600 and is inserted into the tissue.

As shown in FIGS. 23 and 28, the extensions 604 oppose each other and are each configured to move within a respective second channel 506b of the lower housing 304 such that the extensions 604 are each disposed between the lower housing body 494 and a respective guide 376 of the upper housing 308. As shown in FIG. 28, each extension 604 defines a stop 612 that is configured to contact or otherwise abut a respective housing latch 510, such as the protrusion 514 of the housing latch 510, when the needle guard 316 is in the first position so as to maintain the housing latches 510 in interference with the upper housing 308. When the needle guard 316 moves toward the second position, the stops 612 move out of contact with the housing latches 510. The housing latches 510 can then move out of interference with the upper housing 308 so that the upper housing 308 is capable of moving toward the dispensed position. Therefore, the upper housing 308 can be maintained in the pre-use position until the needle guard 36 has been moved to the second position.

With continued reference to FIG. 28, the needle guard 316 further defines an opening 616 in each extension 604 and a needle guard latch 620 that extends up from the extension 604 and into the opening 616. Each needle guard latch 620 is resiliently flexible and defines a groove 624 at its proximal end and a hinge 628 at its distal end. The needle guard latches 620 are configured to flex about their hinges 628 as the needle guard 316 moves from the second position to the final position and when the upper housing 308 is in the dispensed position. As shown in FIG. 28, each needle guard latch 620 defines a sidewall 632 that extends from the hinge 628 to the groove 624. At least a portion of each sidewall 632 that is proximate to the groove 624 is angled relative to the first or second directions. The protrusions 514 of the housing latches 510 can ride along the angled sidewall portions 632 as the upper housing 308 is moved toward the dispensed position so as to cause the needle guard latches 620 to flex and when the needle guard 316 moves from the second position to the final position. When the device 300 is then removed from the tissue and the needle guard 316 moves to the final position the needle guard latches 620 will flex back toward their original positions such that the grooves 624 receive the protrusions 514 of the housing latches 510 to thereby lock the needle guard 316 in the final position.

Figure 29D:
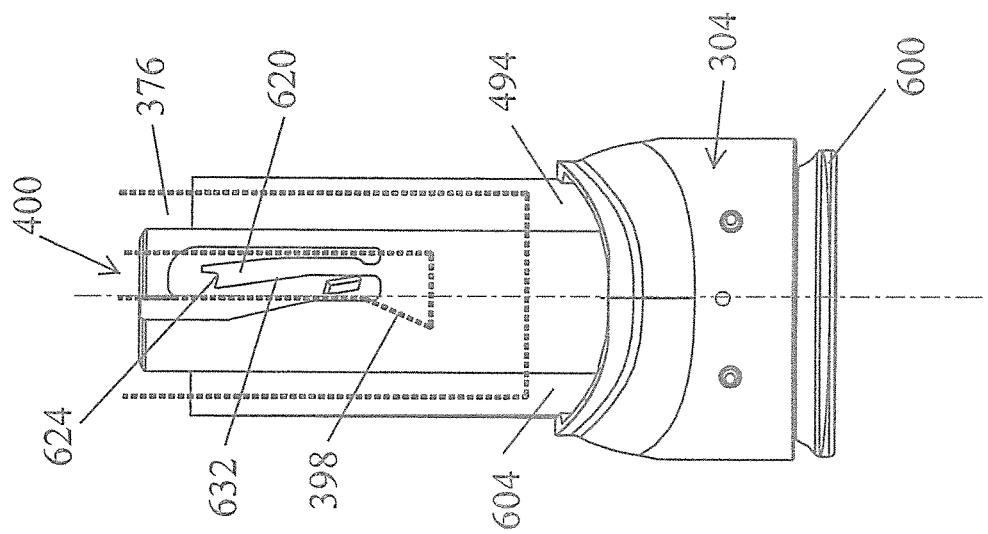
FIG. 29D is a partial front elevation view of the medication delivery device shown in FIG. 29C with the upper housing in the dispensed position.
Figure 29C:
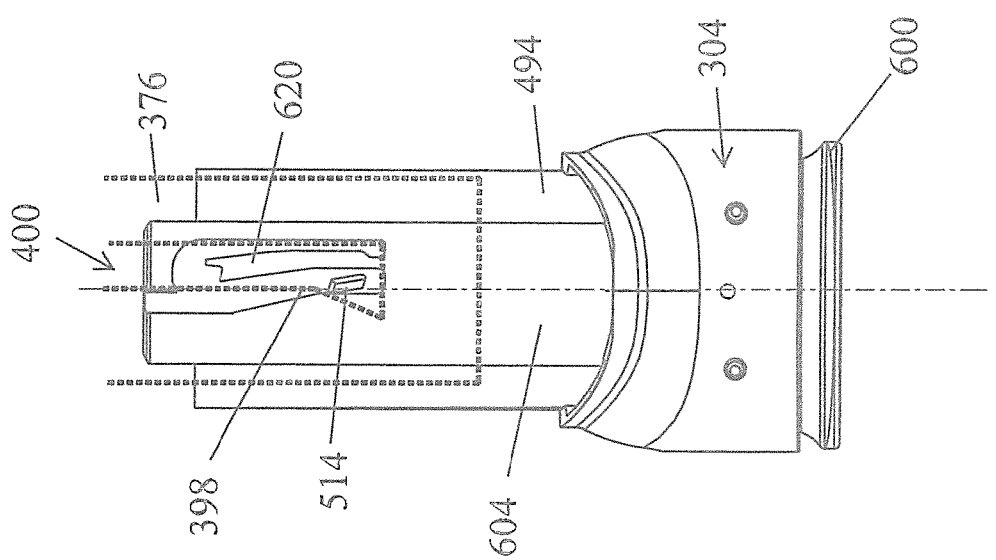
FIG. 29C is a partial front elevation view of the medication delivery device shown in FIG. 29B with the upper housing moving toward the dispensed position and the housing latches being moved into the channels of the upper housing guides.

As shown in FIGS. 29A-29F, the housing latches 510 can be configured to both selectively maintain the upper housing 308 in the pre-use position and later maintain the needle guard 316 in the final position. As shown in FIG. 29A, when the upper housing 308 is in the pre-use position and the needle guard 316 is in the first position, the protrusions 514 of the housing latches 510 abut respective abutment surfaces 398 of the guides 376 of the upper housing 308 so as to prevent the upper housing 308 from moving toward the dispensed position. As shown in FIG. 29A, the stops 612 of the needle guard 316 abut the protrusions 514 and maintain the protrusions 514 interference with the abutment surfaces 398. As shown in FIG. 29B, when the needle guard 316 is moved to the second position, the stops 612 are moved away from the protrusions 514 such that the housing latches 510 are capable of moving out of interference with the abutment surfaces 398 of the upper housing 308 and the upper housing 308 is capable of moving toward the dispensed position. As shown in FIGS. 29C and 29D, as the upper housing 308 moves toward the dispensed position, the protrusions 514 move into and along the channels 400 of the guides 376. As shown in FIG. 29D, the protrusions 514 ride along the angled sidewall portions 632 and cause the needle guard latches 620 to flex so that the protrusions 514 can continue their travel along the channels 400. As shown in FIGS. 29E and 29F, as the needle guard 316 moves from the second position toward the final position the protrusions 514 ride along the sidewalls 632 until the needle guard latches 620 flex back toward their original positions and the grooves 624 receive the protrusions 514 to thereby lock the needle guard 316 in the final position. In this way, the housing latches 510 can be configured to both maintain the upper housing 308 in the pre-use position and lock the needle guard 316 in the final position.

In operation and in reference to FIGS. 30A-30F, the delivery device 300 can be configured to deliver a medication. Prior to use, the upper housing 308 can be locked in the pre-use position by the housing latches 510, and the cap 320 can be coupled to the lower housing 304 so as to shield the needle guard 316 and the needle 332. When the device 300 is ready to be used, the cap 320 can be removed from the lower housing 304 such that the cap 320 removes the needle shield 338 from the needle 332 as shown in FIG. 30B.

As shown in FIG. 30C, the device 300 can be positioned against a skin surface and a manual force can be applied to the upper housing 308 along an insertion direction (e.g. the second direction) such that as the needle guard 316 is pressed against the skin surface, the needle guard 316 moves to the second position and the needle 332 is inserted into the tissue. As the needle guard 316 moves to the second position the stops 612 move out of engagement with the housing latches 510 so that the upper housing 308 is no longer locked in the pre-use position. As shown in FIGS. 30D and 30E, the upper housing 308 can then be moved along the second direction and over the middle housing 312. When the upper housing 308 reaches the dispensed position substantially all of the middle housing 312 is covered by the upper housing 308 and the plunger can be visible within the windows 336 thereby providing visual evidence that all of the medication has been delivered to the tissue.

Further, when the upper housing 308 reaches the dispensed position, the locking latches 390 of the upper housing 308 engage the latch members 530 of the lower housing 304 to thereby lock the upper housing 308 in the dispensed position so as to prevent re-use of the delivery device 300. As the locking latches 390 snap over the latch members 530, an audible click is produced that signifies to the user that the upper housing 308 has reached the dispensed position and is locked in the dispensed position. The upper housing 308 can be permanently locked in the dispensed position such that the device 300 is not reusable. It should be appreciated, however, that the upper housing 308 can be temporarily locked such that the device 300 can be sterilized and reused.

As shown in FIG. 30F, when the device 300 is removed from the skin surface along a direction opposite the insertion direction the needle guard 316 moves along the second direction to the final position. When in the final position, the housing latches 510 interfere with the needle guard latches 620 to thereby lock the needle guard 316 in the final position. In this way, the needle guard 316 can be permanently locked in the final position so that the device 30 is not reusable. It should be appreciated, however, that the needle guard 316 can be temporarily locked such that the device 300 can be sterilized and reused.

As shown in FIGS. 30B and 30F, the needle guard 316 can be configured to move a first distance $d_1$ along the first direction from the first position to the second position and a second distance $d_2$ along the second direction from the second position to the final position. The second distance $d_2$ can be greater than the first distance $d_1$ to thereby signify to the user that the needle guard 316 is in fact in the final position and locked. The needle guard 316, and in particular the housing 600 of the needle guard 316 can include a visual indication 640, such as a color band, at a proximal end of the housing 600 that is only visible when the needle guard 316 is in the final position. It should be appreciated, however, that the needle guard 316 can move any distance from the first position to the second position and any distance from the second position to the final position.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art. This includes a multiple-dose design in which one or both of the upper and middle housings rise to a partial height and deliver a partial syringe when depressed by the user.

What is claimed:

1. A method of injecting a medication from a medication delivery device of the type including an upper housing, a lower housing, a syringe supported by the lower housing and having a needle, and a needle guard supported by the lower housing, the method comprising the steps of:
   placing the medication delivery device against a skin surface so as to cause the needle guard to abut the skin surface, wherein the upper housing is releasably locked with respect to movement toward the needle by a housing latch that interferes with the upper housing;
   applying a force against the upper housing along an insertion direction, thereby causing the skin surface to force the needle guard to retract relative to the lower housing and thereby expose the needle so as to insert the needle into the skin surface;
   during the applying step, causing the housing latch to move out of interference with the upper housing;
   continuing to apply the force against the upper housing along the insertion direction, thereby causing the upper housing to move toward the needle, thereby driving a medication contained within the syringe out of the needle;
   moving the medication delivery device away from the skin surface along a direction opposite the insertion direction so as to remove the needle from the skin surface and cause the needle guard to advance relative to the needle to a final position whereby the needle guard substantially encapsulates the needle; and
   causing the housing latch to lock the needle guard in the final position.

2. The method of claim 1, wherein the continuing step further comprises a step of driving a plunger rod into the syringe so as to drive the medication out of the needle.

3. The method of claim 1, after the continuing step, further comprising a step of preventing the upper housing from retracting away from the needle.

4. The method of claim 1, wherein the medication delivery device further includes a middle housing coupled between the upper housing and the lower housing, wherein the continuing step comprises a step of progressively covering a body of the middle housing with the upper housing to thereby provide a visual indication that the medication is being delivered.

5. The method of claim 4, wherein the continuing step comprises a step of causing a friction member of the upper housing to rub against a friction member of the middle housing as the upper housing progressively covers the body to thereby create a friction force between the upper housing and the middle housing.

6. The method of claim 5, where the friction member of the middle housing is configured as a cantilevered portion, and the continuing step comprises causing the cantilevered portion to flex relative to a central axis of the middle housing as the upper housing moves toward a dispensed position.

7. The method of claim 6, wherein the friction member of the upper housing is a rail, and the continuing step comprises causing the rail to ride along the cantilevered portion.

8. The method of claim 5, wherein the moving step comprises causing a spring to move the needle guard from a second position toward the final position and over the needle as the needle is removed from a tissue, and wherein a frictional force between the friction members of the upper and middle housings is greater than or equal to a force generated by the spring when the needle guard is in the second position.

9. The method of claim 1, wherein:
   the needle guard carries a stop that is configured to abut the housing latch when the needle guard is in a first position so as to maintain the housing latch in interference with the upper housing; and
   the applying step comprises causing the stop to move out of contact with the housing latch as the needle guard moves from the first position to a second position and causing the housing latch to move out of interference with the upper housing.

10. The method of claim 1, wherein the applying step comprises causing the needle guard to move a first distance along the direction opposite the insertion direction when the needle guard is moved from a first position to a second position so as to expose the needle, and the moving step comprises causing the needle guard to move a second distance along the insertion direction when the needle guard is moved to the final position, the second distance being greater than the first distance.

11. The method of claim 1, wherein the causing step comprises causing a needle guard latch of the needle guard to interfere with the housing latch when the needle guard moves to the final position to thereby lock the needle guard in the final position.

12. The method of claim 11, wherein the needle guard latch includes a groove and the housing latch includes a protrusion, and the moving step comprises causing at least one of the needle guard latch and the housing latch to flex toward the other such that the protrusion is received within the groove when the needle guard is in the final position.

13. The method of claim 11, wherein the lower housing includes two housing latches and the needle guard includes two needle guard latches, and wherein the moving step comprises causing each needle guard latch to mate with a respective one of the housing latches when the needle guard moves to the final position.

14. The method of claim 1, wherein the lower housing includes a pair of housing latches and the upper housing includes a pair of guides, and in the placing step, each of the guides abuts a respective housing latch when the upper housing is in a pre-use position to thereby retain the upper housing in the pre-use position.

15. The method of claim 1, wherein the continuing step comprises moving a protrusion of the housing latch in a channel of a guide of the upper housing as the upper housing is moved from a pre-use position towards a dispensed position.

16. The method of claim 15, wherein the guide defines an abutment surface that leads into the channel, and wherein the housing latch interferes with the abutment surface when the upper housing is in the pre-use position.

17. The method of claim 1, comprising a step of inserting the syringe into a syringe retainer of the medication delivery device such that the syringe retainer supports the syringe at a bottom shoulder of the syringe.

18. The method of claim 17, wherein the inserting step comprises causing the syringe to move through a gap between a pair of elastically flexible legs of the syringe retainer towards a seated position such that the syringe causes the elastically flexible legs to move away from each other, and when the syringe is in the seated position, the elastically flexible legs move back toward each other so that tabs of the elastically flexible legs engage the bottom shoulder of the syringe.

19. The method of claim 17, wherein the method comprises a step of inserting the syringe retainer with the syringe into the lower housing such that at least one tab of the syringe retainer abuts the lower housing to thereby lock the syringe retainer within the lower housing.

20. The method of claim 1, wherein the upper housing includes at least one locking latch, the lower housing defines at least one corresponding latch member, and the continuing step comprises causing the at least one locking latch to snap over the at least one latch member to thereby lock the upper housing in a dispensed position.

\* \* \* \* \*